US009611307B2

(12) United States Patent
Girard et al.

(10) Patent No.: US 9,611,307 B2
(45) Date of Patent: Apr. 4, 2017

(54) METHOD FOR INCREASING GRANULOCYTE NUMBER IN A PATIENT BY ADMINISTERING SUPERACTIVE IL-33 FRAGMENTS

(75) Inventors: Jean-Philippe Girard, Rebigue (FR); Corinne Cayrol-Girard, Rebigue (FR); Emma Lefrancais, Mont de Marsan (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 433 days.

(21) Appl. No.: 14/001,271

(22) PCT Filed: Feb. 24, 2012

(86) PCT No.: PCT/EP2012/053199
§ 371 (c)(1),
(2), (4) Date: Nov. 18, 2013

(87) PCT Pub. No.: WO2012/113927
PCT Pub. Date: Aug. 30, 2012

(65) Prior Publication Data
US 2014/0099280 A1    Apr. 10, 2014

(30) Foreign Application Priority Data
Feb. 24, 2011  (FR) ..................... 11 51498

(51) Int. Cl.
| | |
|---|---|
| *A61K 38/20* | (2006.01) |
| *C07K 14/54* | (2006.01) |
| *C07K 16/24* | (2006.01) |
| *G01N 33/68* | (2006.01) |

(52) U.S. Cl.
CPC ............ *C07K 14/54* (2013.01); *C07K 16/244* (2013.01); *G01N 33/6869* (2013.01); *C07K 2319/21* (2013.01); *C07K 2319/50* (2013.01)

(58) Field of Classification Search
CPC ................................ A61K 38/00; A61K 38/20
See application file for complete search history.

(56) References Cited

U.S. PATENT DOCUMENTS 4,816,567 A    3/1989 Cabilly et al.

FOREIGN PATENT DOCUMENTS

| EP | 0 465 529 A1 | 1/1992 |
|---|---|---|
| WO | WO 90/11092 A1 | 10/1990 |
| WO | WO 95/28494 A1 | 10/1995 |
| WO | WO 00/12508 A2 | 3/2000 |
| WO | WO 2005/079844 A2 | 9/2005 |
| WO | WO 2005/085260 A1 | 9/2005 |
| WO | WO 2008/132709 A1 | 11/2008 |

OTHER PUBLICATIONS

Beers and Berkow, The Merck Manual, 17th edition, (1999), pp. 165-177, and pp. 986-995.*
Reeck et al. Cell, vol. 50, p. 667, (1987).*
Cytokine Factsbook (1994), Callard and Gearing, pp. 39-45.*
Adra et al., "Cloning and expression of the mouse pgk-1 gene and the nucleotide sequence of its promoter," Gene, 1987, pp. 65-74, vol. 60, Elsevier Science Publishers B.V.
Ali et al., "Caspase 3 inactivates biologically active full length interleukin-33 as a classical cytokine but does not prohibit nuclear translocation," Biochemical and Biophysical Research Communications, 2010, pp. 1512-1516, vol. 391.
Alves-Filho et al., "Interleukin-33 attenuates sepsis by enhancing neutrophil influx to the site of infection," Nature Medicine, 2010, pp. 708-713, vol. 16, No. 6.
Baekkevold et al., "Molecular Characterization of NF-HEV, a Nuclear Factor Preferentially Expressed in Human High Endothelial Venules," American Journal of Pathology, 2003, pp. 69-79, vol. 163, No. 1.
Buckholz, "Yeast systems for the expression of heterologous gene products," Current Opinion in Biotechnology, 1993, pp. 538-542, vol. 4, Current Biology Ltd.
Burster et al., "Cathepsin G: Roles in antigen presentation and beyond," Molecular Immunology, 2010, pp. 658-665, vol. 47, Elsevier Ltd.
Carriere et al., "IL-33, the IL-1-like cytokine ligand for ST2 receptor, is a chromatin-associated nuclear factor in vivo," PNAS, 2007, pp. 282-287, vol. 104, No. 1.
Cayrol et al., "The IL-1-like cytokine IL-33 is inactivated after maturation by caspase-1," PNAS, 2009, pp. 9021-9026, vol. 106, No. 22.
Chackerian et al., "IL-1 Receptor Accessory Protein and ST2 Comprise the IL-33 Receptor Complex," The Journal of Immunology, 2007, pp. 2551-2555 and cover page, vol. 179, The American Association of Immunologists, Inc.
Edwards et al., "Current applications of COS cell based transient expression systems," Current Opinion in Biotechnology, 1993, pp. 558-563, vol. 4, Current Biology Ltd.
Hajjar et al., "Differences in the substrate binding sites of murine and human proteinase 3 and neutrophil elastase," FEBS Letters, 2007, pp. 5685-5690, vol. 581, Elsevier B.V.
Hazlett et al., "IL-33 Shifts Macrophage Polarization, Promoting Resistance against *Pseudomonas aeruginosa* Keratitis," Invest Ophthalmol Vis Sci, 2010, vol. 51, No. 3, pp. 1524-1532.
Humphreys et al., "IL-33, a Potent Inducer of Adaptive Immunity to Intestinal Nematodes," Journal of Immunology, 2008, pp. 2443-2449 and cover page, vol. 180, The American Association of Immunologists, Inc.

(Continued)

*Primary Examiner* — Prema Mertz
(74) *Attorney, Agent, or Firm* — Crowell & Moring LLP

(57) ABSTRACT

The present invention discloses novel active polypeptide fragments of human IL-33 corresponding to natural forms generated by the proteases of human neutrophils (cathepsin G, elastase 2, proteinase 3), as well as the use thereof as a drug, in particular for the treatment of infectious diseases, inflammatory diseases, atherosclerosis, cardiovascular diseases, obesity, or cancer.

7 Claims, 10 Drawing Sheets

(56) References Cited

OTHER PUBLICATIONS

Figure 1:
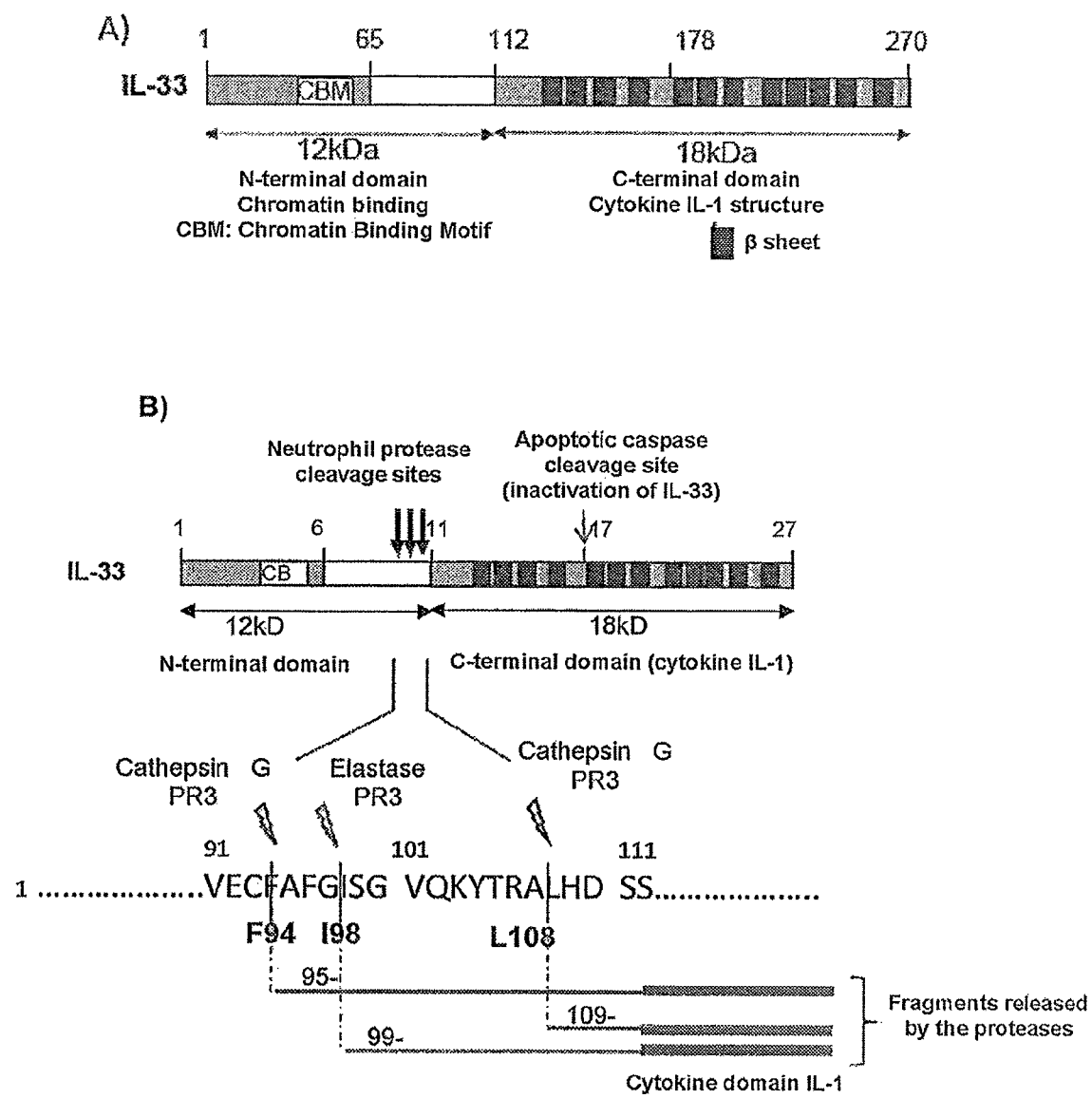

Köhler et al., "Continuous cultures of fused cells secreting antibody of predefined specificity," Nature, 1975, pp. 495-497, vol. 256.

Korkmaz et al., "Neutrophil Elastase, Proteinase 3, and Cathepsin G as Therapeutic Targets in Human Diseases," Pharmacological Reviews, 2010, pp. 726-759, vol. 62, No. 4, The American Society for Pharmacology and Experimental Therapeutics.

Kurowska-Stolarska et al., "Interleukin-33: a novel mediator with a role in distinct disease pathologies," Journal of Internal Medicine, 2010, pp. 29-35, vol. 269, The Association for the Publication of the Journal of Internal Medicine.

Liew et al., "Disease-associated functions of IL-33: the new kid in the IL-1 family," Nature Reviews, 2010, pp. 103-110, vol. 10, Macmillan Publishers Limited.

Lingel et al., "Supplemental Data: Structure of IL-33 and Its Interaction with the ST2 and IL-1RacP Receptors—Insight into the Heterotrimeric IL-1 Signaling Complexes," Structure, 2009, thirteen pages, vol. 17.

Luckow et al., "Efficient Generation of Infectious Recombinant Baculoviruses by Site-Specific Transposon-Mediated Insertion of Foreign Genes into a Baculovirus Genome Propagated in *Escherichia coli*," Journal of Virology, 1993, pp. 4566-4579, vol. 67, No. 8, American Society for Microbiology.

Miller et al., "Interleukin-33 Induces Protective Effects in Adipose Tissue Inflammation During Obesity in Mice," Circ. Res., 2010, pp. 650-658, vol. 107.

Miller et al., "IL-33 reduces the devlopment of atherosclerosis," The Journal of Experiemental Medicine, 2008, pp. 339-346, vol. 205, No. 2, The Rockefeller University Press.

Moessler et al., "The SM 22 promoter directs tissue-specific expression in arterial but not in venous or visceral smooth muscle cells in transgenic mice," Development, 1996, pp. 2415-2425, vol. 122, The Company of Biologists Limited.

Moussion et al., "The IL-1-Like Cytokine IL-33 Is Constitutively Expressed in the Nucleus of Endothelial Cells and Epithelial Cells In Vivo: A Novel 'Alarmin'?," PLoS one, 2008, pp. 1-8, vol. 3, Issue 10.

Nufer et al., "Amino-Terminal Processing of Chemokine ENA-78 Regulates Biological Activity," Biochemistry, 1999, pp. 636-642, American Chemical Society.

Pushparaj et al., "The cytokine interleukin-33 mediates anaphylactic shock," PNAS, 2009, pp. 9773-9778 with Retraction and Correction, vol. 106, No. 24.

Rankin et al., "IL-33 Induces IL-13-Dependent Cutaneous Fibrosis," The Journal of Immunology, 2010, pp. 1526-1535 with cover page, vol. 184.

Reen, "Enzyme-Linked Immunosorbent Assay (ELISA)," Methods in Molecular Biology, 1994, pp. 461-466, vol. 32, Humana Press Inc.

Sambrano et al., "Cathepsin G Activates Protease-activated Receptor-4 in Human Platelets," The Journal of Biological Chemistry, 2000, pp. 6819-6823, vol. 275, No. 10, The American Society for Biochemistry and Molecular Biology, Inc.

Schmitz et al., "IL-33, an Interleukin-1-like Cytokine that Signals via the IL-1 Receptor-Related Protein ST2 and Induces T Helper Type 2-Associated Cytokines," Immunity, 2005, pp. 479-490, vol. 23.

Seki et al., "Interleukin-33 Prevents Apoptosis and Improves Survival After Experimental Myocardial Infarction Through ST2 Signaling," Circulation Heart Failure, 2009, pp. 684-691 with cover page, vol. 2, American Heart Association.

Sims et al., "The IL-1 family: regulators of immunity," Nature Reviews, 2010, pp. 89-102, vol. 10, Macmillan Publishers Limited.

Stolarski et al., "IL-33 Exacerbates Eosinophil-Mediated Airway Inflammation," The Journal of Immunology, 2010, pp. 3472-3480 with cover page, vol. 185.

Talabot-Ayer et al., "Protein Synthesis, Post-Translational Modification, and Degradation: Interleukin-33 Is Biologically Active Independently of Caspase-1 Cleavage," The Journal of Biological Chemistry, 2009, pp. 19420-19426 with cover page, vol. 284.

Tatusova et al., "BLAST 2 Sequences, a new tool for comparing protein and nucleotide sequences," FEMS Microbiology Letters, 1999, pp. 247-250, vol. 174.

Xu et al., "IL-33 Exacerbates Autoantibody-Induced Arthritis," The Journal of Immunology, 2010, pp. 2620-2626 with cover page, vol. 184, The American Association of Immunologists, Inc.

Labbaye et al., "Wegener autoantigen and myeloblastin are encoded by a single mRNA," Proc. Natl. Acad. Sci., 1991, pp. 9253-9256, vol. 88, Medical Sciences.

Rao et al., "Characterization of Proteinase-3 (PR-3), a Neutrophil Serine Proteinase," The Journal of Biological Chemistry, 1991, pp. 9540-9548, vol. 266, No. 15, The American Society for Biochemistry and Molecular Biology.

Lüthi et al., "Suppression of Interleukin-33 Bioactivity through Proteolysis by Apoptotic Caspases," Immunity, 2009, pp. 84-98, vol. 31, Elsevier Inc.

International Search Report dated Jun. 19, 2012 with English translation (nine (9) pages).

International Preliminary Report on Patentability (PCT/IB/373) including Written Opinion (PCT/ISA/237) dated Aug. 27, 2013 with English translation (fifteen (15) pages).

Bieth, "Les élastases," J. Soc. Biol., 2001, pp. 173-179, vol. 195, No. 2.

Kargi et al., "Elastase and cathepsin G of human monocytes : heterogeneity and subcellular localization to peroxidase-positive ganules," Journal of Histochemistry & Cytochemistry, 1990, pp. 1179-1186 with cover page, vol. 38, No. 8.

Hausman et al., "The cell: a molecular approach," The Chemistry of Cells, 2004, p. 51, ASM Press.

Olins et al., "Recent advances in heterologous gene expression in *Escherichia coli*," Current Opinion in Biotechnology, 1993, pp. 520-525, vol. 4, Monsanto Corporate Research.

Furth et al., "Gene Transfer into Somatic Tissues by Jet Injection," Analytical Biochemistry, 1992, pp. 365-368, vol. 205, No. 2.

Ishioka et al., "Utilization of MHC Class I Transgenic Mice for Development of Minigene DNA Vaccines Encoding Multiple HLA-Restricted CTL Epitopes," The Journal of Immunology, 1999, pp. 3915-3925 with cover page, vol. 162.

Rao et al., "Proteinase-3 (PR-3): A Polymorphonuclear Leukocyte Serine Proteinase," Annals New York Academy of Sciences, 1991, pp. 60-68, vol. 624.

Jose C. Alves-Filho et al., "Interleukin-33 attenuates sepsis by enhancing neutrophil influx to the side of infection", Nature Medicine, vol. 16, No. 5, Jun. 2010, pp. 708-712: page doi:10.1038/nm. 2156.

Jeffrey Crawford et al., "Reduction by Granulocyte Colony-Stimulating Factor of Fever and Neutropenia Induced by Chemotherapy in Patients with Small-Cell Lung Cancer", The New England Journal of Medicine, Jul. 18, 1991, pp. 164-170.

Hrishikesh M. Mehta et al., "G-CSF and GM-CSF in Neutropenia", The Journal of Immunology, 2015; 195: 1341-1349.

Thomas J. Smith et al., "2006 Update of Recommendations for the Use of White Blood Cell Growth Factors: An Evidence-Based Clinical Practice Guideline", Journal of Clinical Oncology, vol. 24, No. 19, Jul. 1, 2006; pp. 3187-3205.

Emma Di Carlo et al., "The intriguing role of polymorphonuclear neutrophils in antitumor reactions", Blood, Jan. 15, 2001, vol. 97, No. 2, pp. 339-345.

\* cited by examiner

A)

B)

Figure 4 (Continued)

Tot = Total; NF = Non-Fixed; Lav = Wash; Elu = Elution; Throm = Thrombin; Gel Filtr = Gel Filtration; Viv = Vivaspin

| Recombinant Proteins | Quantity obtained per litre of culture | Endotoxin dosage |
|---|---|---|
| Human IL-33 $_{1\text{-}270}$ | <1 µg | |
| Human IL-33 $_{95\text{-}270}$ | 16 mg | 0,01 U/µg |
| Human IL-33 $_{99\text{-}270}$ | 11 mg | 0,008 U/µg |
| Human IL-33 $_{109\text{-}270}$ | 9 mg | 0,004 U/µg |

METHOD FOR INCREASING GRANULOCYTE NUMBER IN A PATIENT BY ADMINISTERING SUPERACTIVE IL-33 FRAGMENTS

INTRODUCTION

Cytokines of the interleukin 1 family (IL-1) play a major role in a large number of autoimmune, infectious and inflammatory diseases (Sims J E and Smith D E, *Nature Rev Immunology* 2010). Interleukin 33 (IL-33), initially named NF-HEV, is a new cytokine of the IL-1 family comprising 270 amino acids (FIG. 1, NP_254274, SEQ ID NO: 1). It is a nuclear factor strongly expressed in the cuboidal endothelial cells (Bakkevold E et al., *American Journal Pathology* 2003). IL-33 has, in its carboxy-terminal portion, structural homologies with interleukin 1 (structure with 12 beta sheets) (Lingel et al., *Structure* 2009) and binds with the orphan receptor ST2 (IL1-R4) (Chackerian A A et al., *Journal of Immunology* 2007). IL-33 is a nuclear protein associated with chromatin (Carriere V et al., *PNAS* 2007). It is expressed constitutively in the endothelial cells of the blood vessels of most tissues, as well as in epithelial cells of tissue exposed to the environment, such as the skin, the stomach, the salivary glands or the lungs (Moussion et al., *PLoS ONE* 2008).

It is known that IL-33 is released in its biologically active whole form (IL-33$_{aa1-270}$, in the event of cell damage or necrosis. Whole IL-33 is indeed capable of binding to the ST2 receptor (Cayrol and Girard, PNAS 2009) and of activating the target cells, in particular the cells of the immune system: the Th2 lymphocytes, the mastocytes, the NK and iNKT killer cells, the basophils and the eosinophils (for review, see Liew et al., *Nature Rev Immunology* 2010). The activation of the ST2 receptor on the target cells induces, depending on the cells, the secretion of Th2 cytokines (IL-4, IL-5, IL-13) and/or pro-inflammatory cytokines (TNF-$\alpha$, IL-1, IFN-$\gamma$). In addition, several recent studies have shown the capacity of IL-33 for recruiting immune system cells, such as neutrophils (Alves-Filho et al., *Nature Medicine* 2010) at inflammatory or infectious sites. According to these results, IL-33 could therefore serve as a danger signal for alerting the immune system after infection or trauma of endothelial or epithelial cells (Moussion et al., *PLoS ONE* 2008; Cayrol and Girard, *PNAS* 2009).

IL-33 has a protective effect in certain pathologies, whereas it is an aggravation factor in others. For example, IL-33 has a protective role in infectious diseases such as sepsis (Alves-Filho et al., *Nature Medicine* 2010), *Pseudomonas keratitis* (Hazlett et al., *Invest Ophtalmol Vis Sci.* 2010) or nematode infection (Humphreys et al., *Journal of Immunology* 2008). This protective role is also demonstrated in atherosclerosis (Miller et al., *J. Exp. Med.* 2008), myocardial infarction (Seki et al., *Circ Heart Fail* 2009), adipose tissue inflammation in obesity (Miller et al., *Circ Res* 2010) and cancer (WO 2005/079844). This data suggests that IL-33 could be used as a therapeutic agent for these pathologies. By contrast, it was demonstrated that IL-33 exacerbated the physiopathological effects in other types of diseases such as rheumatoid arthritis (Xu et al., *Journal of Immunology* 2010), allergic inflammation of the airways such as asthma (Stolarski et al., *Journal of Immunology* 2010), cutaneous fibrosis (Rankin et al., *J. Immunol.* 2010) or anaphylactic shock (Pushparaj et al., *PNAS* 2008), making IL-33 a potential therapeutic target for these pathologies.

Thus, these studies have shown, both in humans and in animal models, that the in vivo administration of IL-33 could promote recovery from numerous diseases, in particular chronic inflammatory diseases, allergic diseases, cardiovascular diseases, infectious diseases, cancer and Alzheimer's disease (for review, see Liew et al., *Nature Rev Immunology* 2010).

It should be noted that the authors of the different studies mentioned above have used, for their in vivo studies, an artificially truncated form of IL-(IL-33$_{aa112-270}$) which contains the "cytokine IL-1" domain of IL-33 (amino acids 112 to 270), and which lacks the N-terminal domain of the whole protein (amino acids 1 to 111) (cf. FIG. 1A). The scientific community has long believed that this truncated form IL-33$_{aa112-270}$ could be generated in vivo. Indeed, it was suggested that a form IL-33$_{aa112-270}$, corresponding to the "Cytokine IL-1"-type C-terminal domain, could be generated after the cleavage of IL-33 by caspase 1 after the residue Sethi (Schmitz et al., *Immunity* 2005); it was considered since then that the maturation of IL-33 by caspase 1 was possible, producing the active truncated form (IL-33$_{aa112-270}$). However, it was recently established that cleavage by caspases results not in activation but in inactivation of the protein, because these proteases cleave the IL-33 protein in the cytokine IL-1 domain, between the 4th and 5th $\beta$ sheets, at the level of the DGVD sequence (aa175-178). The cleavage of IL-33 by the apoptotic caspases could be a mechanism selected to eliminate the pro-inflammatory activities of IL-33 during apoptosis, a process that does not lead to in vivo inflammation. An even more important result is that it was demonstrated that the mature form IL-33$_{aa112-270}$ used in numerous studies, was not generated by the action of caspase 1 in vitro and therefore, a fortiori, in vivo. This truncated form IL-33$_{aa112-270}$ therefore does not exist in vivo (Cayrol and Girard, PNAS 2009, Lüthi et al., *Immunity* 2009; Talabot-Ayer et al., *J. Biol. Chem.* 2009; Ali et al., *Biochem Biophys Res Commun* 2010), and therefore was never encountered by the human immune system. Its use in human therapy could therefore present significant problems, in particular of immunogenicity. The use of a natural form of IL-33 is preferable for applications in human therapy. However, it has not, to date, been possible to express the whole IL-33 protein in quantities compatible for performing in vivo tests, and even less so with the industrial production of a biotherapeutic drug.

It was therefore required to identify an active form of human IL-33, which i) is active, at least as much as or more active than the whole form, ii) is generated naturally (and therefore a priori has little or no immunogenicity), and iii) can be produced on a large scale in recombinant form (by milligrams or even grams) so as to be used as a medium- and long-term treatment in humans.

However, no protease capable of inducing the maturation of human IL-33, naturally, in a more active form than the whole form, had been identified so far.

The present inventors responded to this need, by demonstrating that whole IL-33 is cleaved naturally by three neutrophil proteases, human cathepsin G, elastase and proteinase 3. These proteases release carboxy-terminal fragments of larger size than the artificially truncated form IL-33$_{aa112-270}$, said fragments having a superior biological activity, as much in vitro as in vivo, to that of the whole form IL-33$_{aa1-270}$. Unlike the form IL-33$_{aa1-270}$, these new fragments of IL-33 are easily expressed in bacterial cells such as *E. Coli*. They have the advantage of being obtained naturally, and are more active in vivo than the artificially truncated form of IL-33 used until now (IL-33$_{aa112-270}$) (cf. example d below).

Due to their properties, these new fragments of IL-33 could be produced in the biotechnology industries in order to be used in particular in human health (treatments of human diseases in which IL-33 has a protective effect) or for scientific research.

KEY TO THE FIGURES

FIG. 1A describes the primary structure of the whole human protein IL-33. The functional domains (chromatin binding, cytokine IL-1) are indicated. FIG. 1B shows the sites of cleavage by the neutrophil proteases cathepsin G (Cat G), Elastase 2 (Elastase) and Protease 3 (pR3) upstream of the "cytokine IL-1"-type C-terminal domain, as well as the fragments released by the action of these proteases (fragments IL-33$_{aa95-270}$, IL-33$_{aa99-270}$ and IL-33$_{aa109-270}$).

Figure 2:
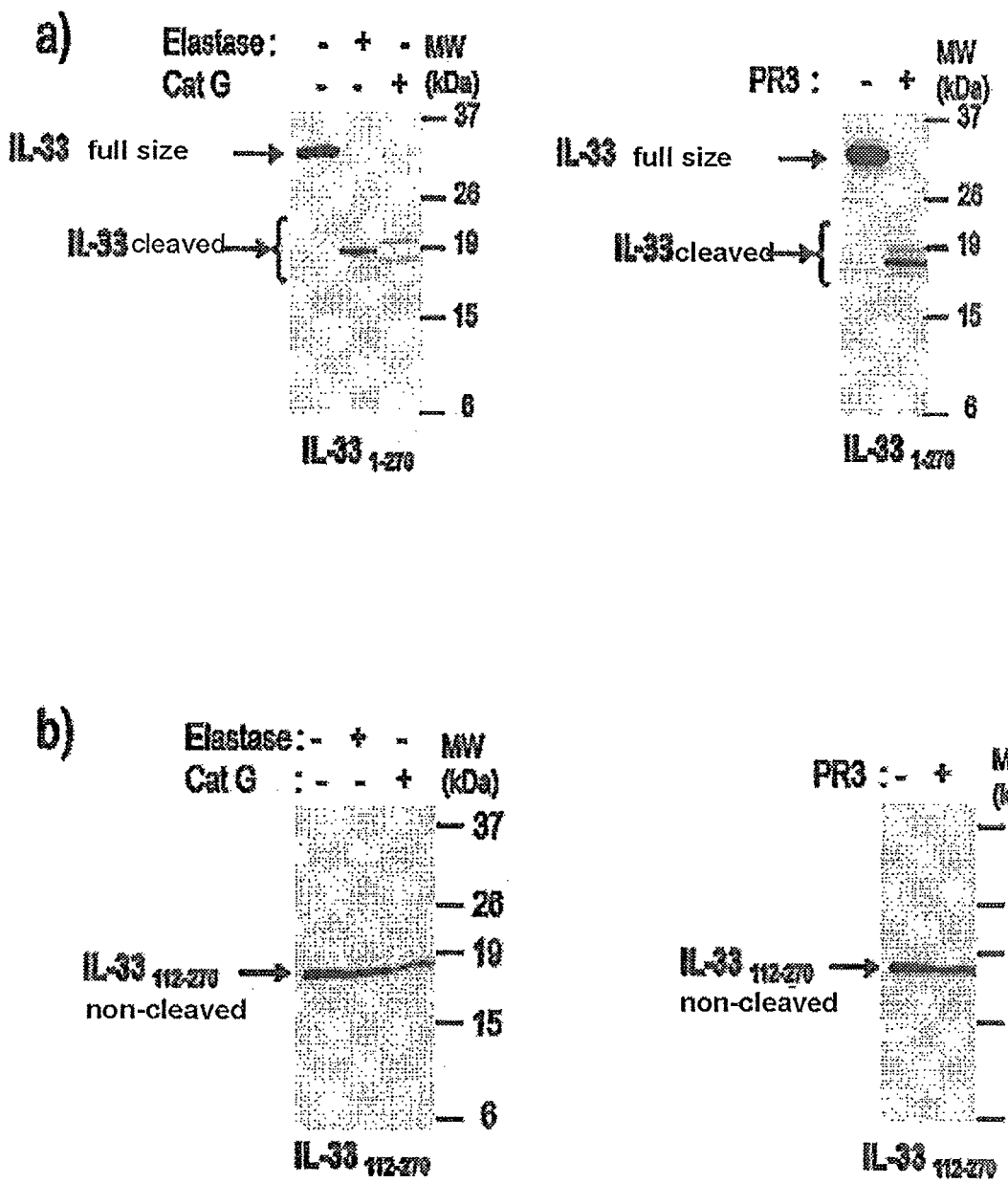
Figure 2:
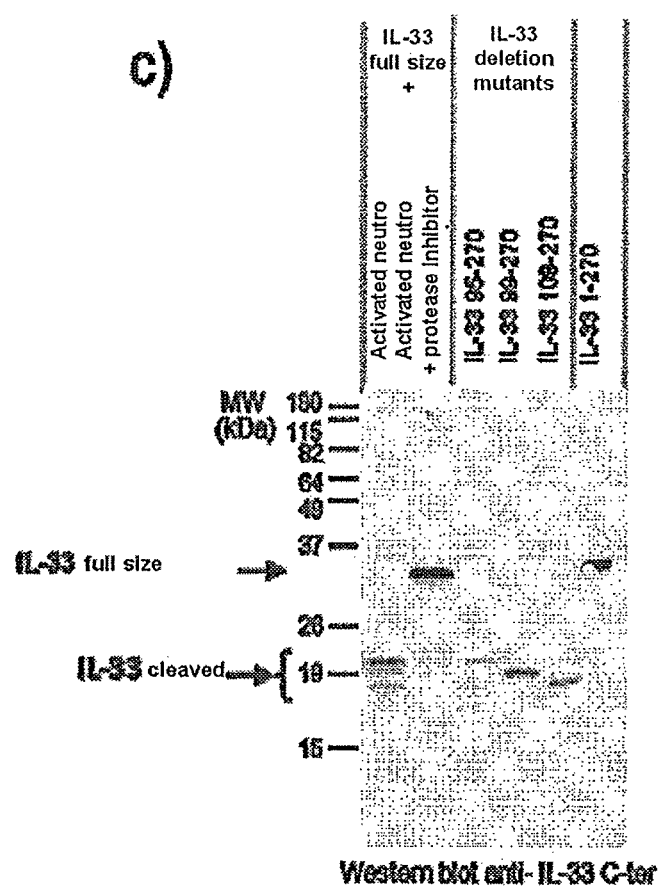
Figure 2:
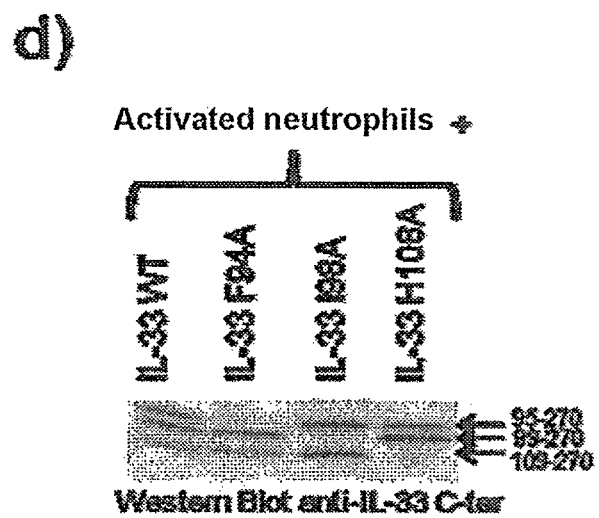

FIG. 2A shows the results of the western blots demonstrating that the whole human interleukin IL-33 is cleaved in vitro by the recombinant proteases Cathepsin G (Cat G), Elastase 2 (Elastase) and Protease 3 (PR3), by contrast with the truncated form IL-33$_{aa112-270}$, which remains intact in the presence of these proteases (FIG. 2B). FIG. 2C shows the results demonstrating that human IL-33 is the substrate of these same human proteases extracted directly from human neutrophils ex vivo. FIG. 2D shows that the fragments IL-33$_{aa95-270}$, IL-33$_{aa99-270}$ and IL-33$_{aa109-270}$ are not released by the neutrophil proteases when the corresponding cleavage sites are mutated.

Figure 3:
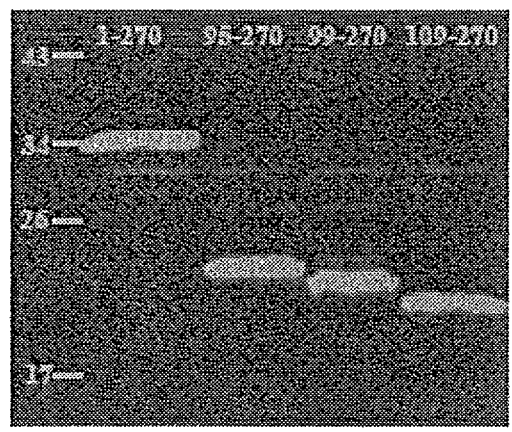
Figure 3:
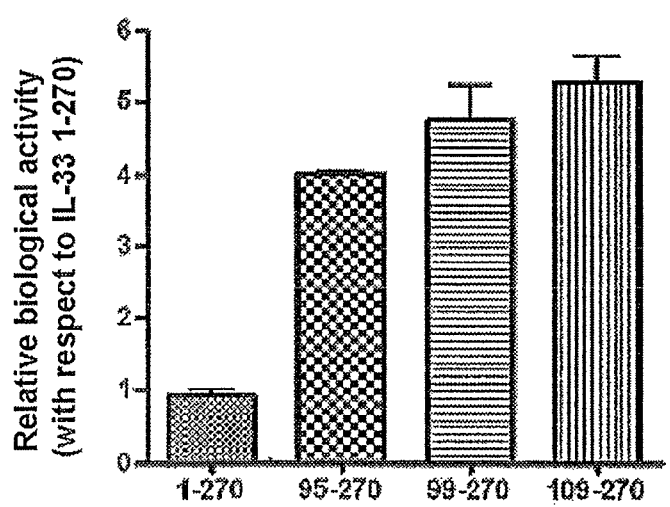

FIG. 3A shows the quantitative analysis of the recombinant proteins IL-33$_{aa1-270}$, IL-33$_{aa95-270}$, IL-33$_{aa99-270}$ and IL-33$_{aa109-270}$ by western blot, while FIG. 3B shows the activity of these different proteins in vitro on the secretion of IL-6 by MC/9 mast cells.

Figure 4:
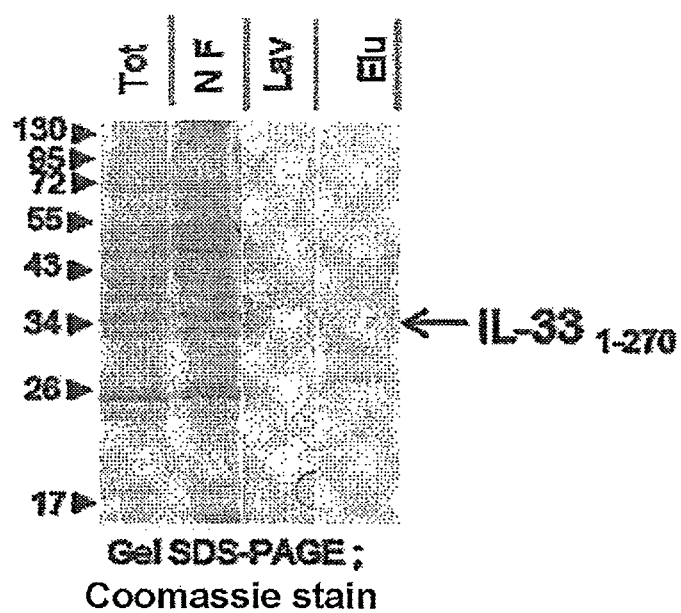
Figure 4:
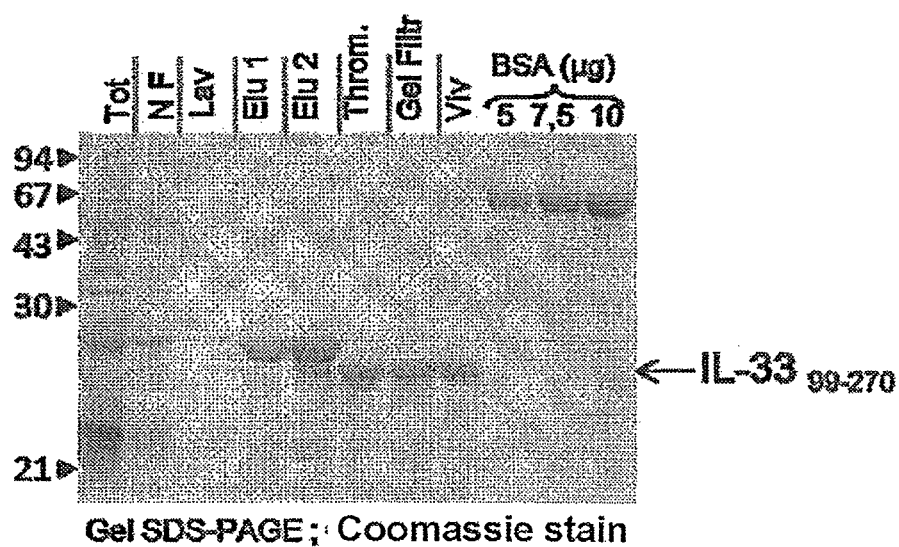
Figure 4:
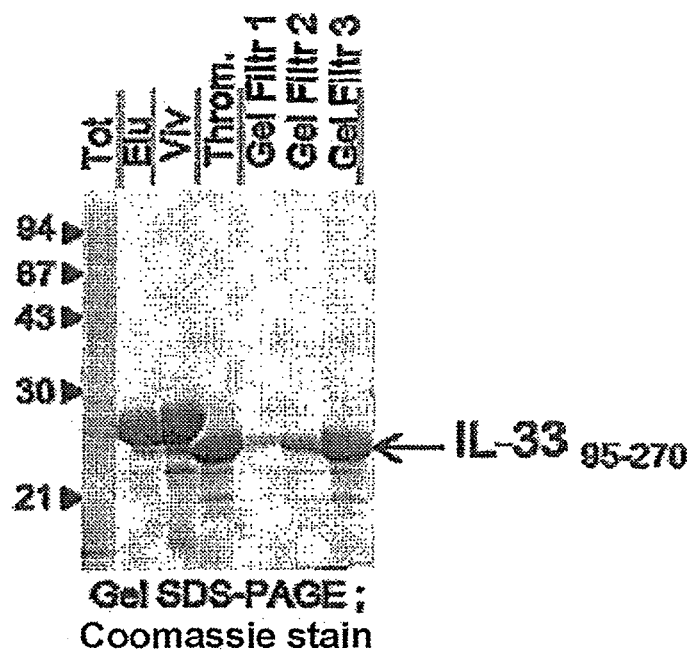
Figure 4:
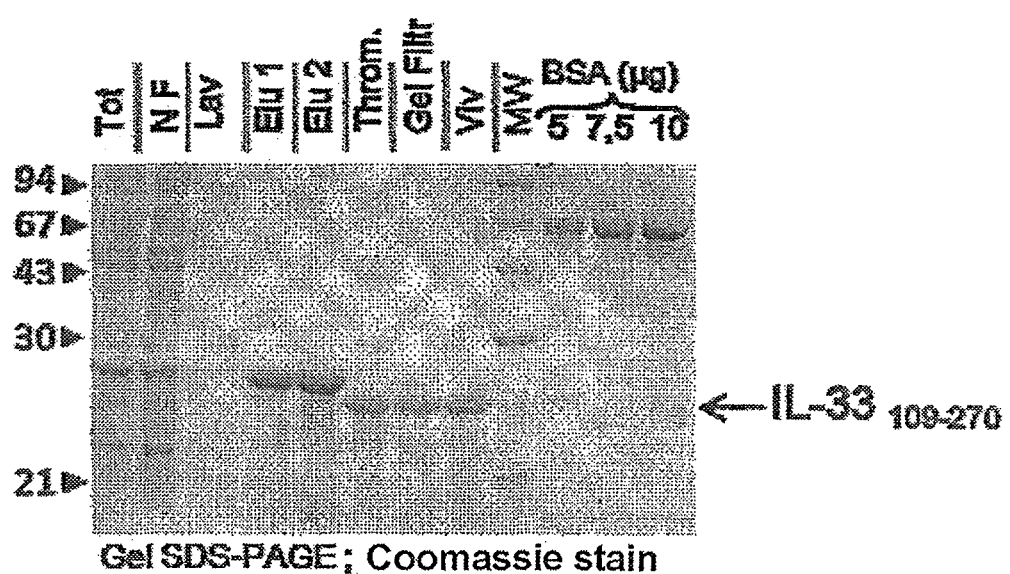

FIG. 4 shows the expression profiles of the three polypeptide fragments of the invention, IL-33$_{aa95-270}$, IL-33$_{aa99-270}$ and IL-33$_{aa109-270}$ obtained by recombinant means in bacterial cells (the vector used is the vector pET15b and the E. coli strain is the strain BL21; for more details, see example c below). Several milligrams of purified recombinant protein were obtained from a liter of E. coli culture (cf. table).

Figure 5:
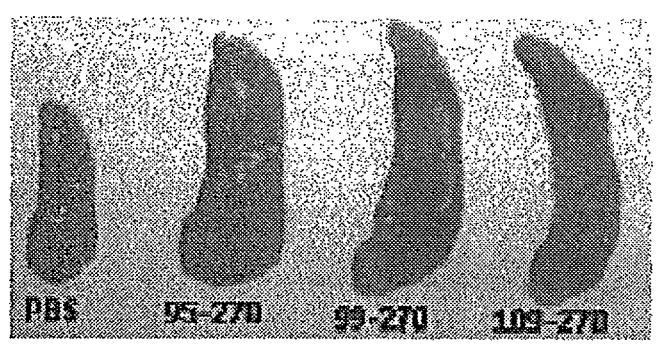
Figure 5:
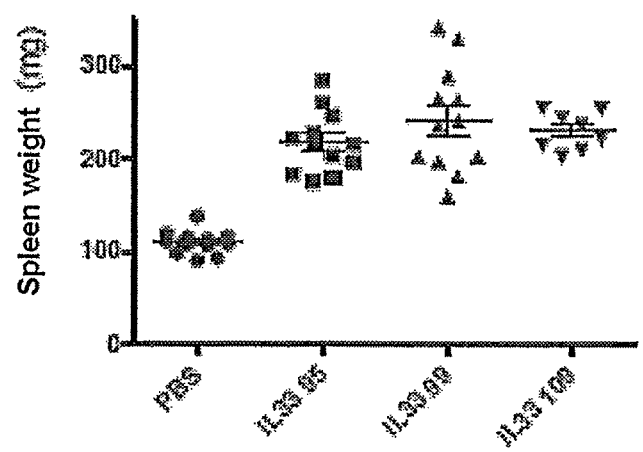
Figure 5:
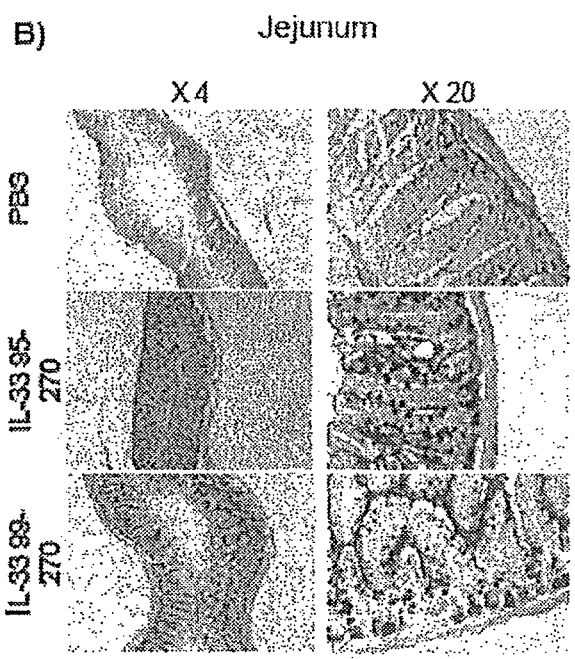
Figure 5:
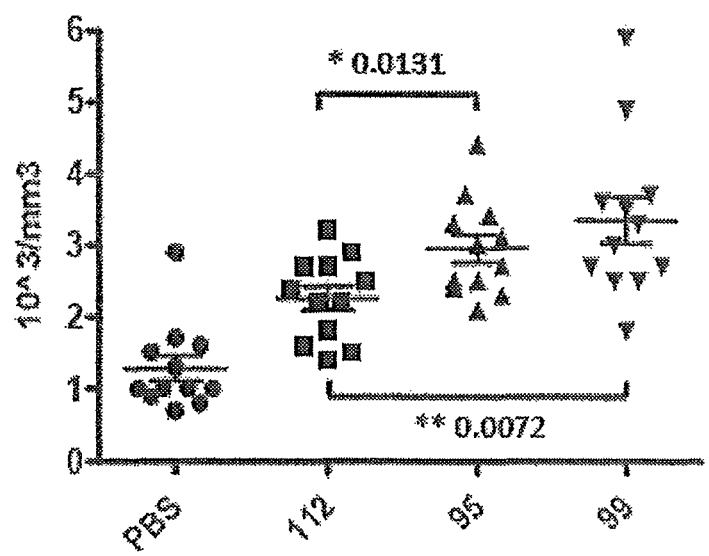

FIG. 5 shows the results obtained in vivo with the polypeptide fragments of the invention. The spleens of mice having received a daily injection of these fragments for 7 days were sampled (A) and the jejunum was analysed by PAS-Alcian blue stain (B). The number of granulocytes in the blood was measured after 7 days (C).

DESCRIPTION OF THE INVENTION

The objective of this invention was to identify an active fragment of human IL-33 (at least as active or more active than the whole form, and preferably at least as active as IL-33$_{aa112-270}$) which corresponds to a natural form (and therefore a priori with little or no immunogenicity) and which can be produced on a large scale in recombinant form (on the order of the milligram or the gram) and therefore be capable of being used for health applications (medium- and long-term treatments in humans) and in biotechnology (scientific research).

Neutrophils are the first circulating leukocytes to migrate to the inflammation site and constitute the first line of defence against pathogenic agents. Aside from their role as phagocytes, they can provide an innate defence by releasing granular proteins, in particular the proteases Cathepsin G, Elastase 2 or Proteinase 3, in the extracellular environment.

The present inventors were able to demonstrate, for the first time, that the action of cathepsin G or proteinase 3 of leukocytes releases the polypeptide fragments IL-33$_{aa95-270}$ and IL-33$_{aa99-270}$ of the N-terminal domain of human IL-33. The action of the neutrophil elastase 2 or of the protease 3 releases the polypeptide fragment IL-33$_{aa99-270}$ of the N-terminal domain of human IL-33. The cleavage sites of these proteases have been determined very precisely, thus showing three new IL-33 fragments, IL-33$_{aa95-270}$ IL-33$_{aa99-270}$ and IL-33$_{aa109-270}$, which had never been identified to date (cf. FIGS. 1B and 2). By contrast with the fragment IL-33$_{aa112-270}$ used heretofore, these fragments result from the natural cleavage of whole IL-33 by the neutrophil proteases in humans, and are therefore physiological.

Surprisingly, these fragments of IL-33 (IL-33$_{aa95-270}$, IL-33$_{aa99-270}$ and IL-33$_{aa109-270}$) have, in vitro and in vivo, a biological activity superior to the whole form of human IL-33 and/or to the truncated form IL-33$_{aa112-270}$ used until now: indeed, these three new IL-33 fragments induce, in vitro, the secretion of four times more IL-6 than the whole form of IL-33 in a murine MC/9 mast cell line (FIG. 3B) and a daily injection of peptides in mice for 7 days leads to an inflammatory reaction involving a doubling of the weight of the spleen after 7 days, and a significant increase in the number of granulocytes (predominantly neutrophils) in the blood of mice, with respect to the truncated form IL-33$_{aa112-270}$ (cf. example d below).

Finally, by contrast with the whole form of human IL-33, these polypeptide fragments of IL-33 (IL-33$_{aa95-270}$, IL-33$_{aa99-270}$ and IL-33$_{aa109-270}$) are easily expressed by the cells classically used for the production of recombinant proteins (E. coli cells, for example), and levels of 9 mg per liter of cell culture are obtained (see example c below).

In a first aspect, the present invention thus relates to an isolated polypeptide fragment of human interleukin 33 (hIL-33), biologically active, chosen from the fragments having, as a sequence, amino acids 95 to 270 (SEQ ID NO: 2), 99 to 270 (SEQ ID NO: 3) or 109 to 270 (SEQ ID NO: 4) of human interleukin 33 (hIL-33), said fragments being natural products of hIL-33 cleavage by at least one protease of human neutrophils.

In a particular embodiment of the invention, said protease of human neutrophils is chosen from the group consisting of: cathepsin G, leukocyte proteinase 3, and neutrophil elastase 2.

More specifically, the present invention relates to the polypeptide fragment IL-33$_{aa95-270}$ having the sequence SEQ ID NO: 2, which is a natural product of hIL-33 cleavage by cathepsin G and proteinase 3 of the leukocytes, the polypeptide fragment IL-33$_{aa99-270}$ having the sequence SEQ ID NO: 3, which is a natural product of hIL-33 cleavage by proteinase 3 of the leukocytes and neutrophil elastase 2, and finally the polypeptide fragment IL-33$_{aa109-270}$ having the sequence SEQ ID NO: 4, which is a natural product of hIL-33 cleavage by Cathepsin G and proteinase 3 of the leukocytes.

These three fragments therefore result from the cleavage of whole human IL-33 by proteases naturally present in humans, and are therefore natural. They can be generated naturally in humans and therefore are not a priori immunogenic. In other words, these fragments can be recognized as self antigens by the human immune system, and therefore do not trigger, when they are injected into human beings, an immune reaction targeted at their own rejection. They are therefore tolerated by the individuals into whom they are injected, over the short, medium and long term (typically, for the entire lifetime of the patient). It is recalled here that the non-immunogenicity of the polypeptide fragment of the invention in no way weakens its ability to stimulate and recruit the cells of the immune system (Th2 lymphocytes, mastocytes, NK and iNKT, basophils and eosinophils) of the individual into whom it is injected, like the whole interleukin IL-33.

"Cathepsin G" in the present invention refers to an enzyme belonging to the family of S1 proteases (or S1 peptidases). Its enzymatic activity is preferably characterized by the number EC 3.4.21.20. It is in particular capable of cleaving chemokines such as CXCL5 (Nufer O et al., *Biochemistry* 1999) or membrane receptors such as PAR4 (Sambrano G R et al., *J. Biol. Chem.* 2000). It has a catalytic triad (serine, histidine and aspartate), characteristic of mammal serine proteases. The compilation of different data has made it possible to define preferential cleavage sites (Burster T et al. *Molecular Immunology* 2010). Characteristically, aromatic residues (Phe, Tyr) or charged residues (Lys, Arg) are often found in position P1 (position of the amino acid located just upstream of the cleaved bond) (Korkmaz B et al., *Pharmacological Reviews* 2010). This enzyme is preferably found in the azurophilic granules of the polymorphonuclear neutrophil leukocytes. It is involved in the destruction and digestion of pathogens present in the connective tissue or at inflammation sites (Kargi H A et al., *J. Histochem. Cytochem* 1990). In humans, it is coded by the CTSG gene. It preferably has the sequence described under accession number HUMCAPG J04990.1. Even more preferably, it has the sequence SEQ ID NO: 6. The present inventors were able to demonstrate, for the first time, that the action of cathepsin G of sequence SEQ ID NO: 6 releases the polypeptide fragments IL-33$_{aa95-270}$ and IL-33$_{aa109-270}$ of the N-terminal domain of human IL-33.

"Leukocyte proteinase 3" in the terms of the present invention refers to myeloblastin, neutrophil proteinase 4, azurophilic granule protein 7 or the Wegener granulomatosis autoantigen. It will be referred to as "proteinase 3" (PRTN3) in the context of the present application. Its enzymatic activity is preferably characterized by the number EC 3.4.21.76. This enzyme, also belonging to the family of S1 proteases, is capable of hydrolysing proteins, and in particular elastin (Rao N V et al., *PNAS* 1991). The preferential substrates of PR3 have, in position P1, hydrophobic amino acids (Val, Cys, Ala, Met, Leu, Ser) (Korkmaz et al., *Pharmacological Reviews* 2010) or polar amino acids (Asn, Cys, Glu, Gln, Ser, Thr, Trp, Tyr) (Hajjar E et al., *FEBS Letters* 2007). Preferably, the proteinase 3 used in the invention is the human enzyme, for example that referenced under accession number NCBI_NP002768.3. Even more preferably, the proteinase 3 used in the invention has the sequence SEQ ID NO: 7. The present inventors were able to demonstrate that the action of the protease 3 of sequence SEQ ID NO: 7 on human IL-33 releases the polypeptide fragments IL-33$_{aa95-270}$, IL-33$_{aa109-270}$ and IL-33$_{aa99-270}$.

"Neutrophil elastase 2" in the terms of the present invention refers to medullasin or even leukocyte elastase, coded by the ELANE gene. It will be referred to as "elastase 2" in the context of the present application. Its enzymatic activity is preferably characterized by the number EC 3.4.21.37. This enzyme is capable of cleaving elastin (Bieth J G, *J. Soc. Biol.* 2001). Concerning the specific cleavage sites, a preference for small hydrophobic residues in position P1 is noted (Val, Cys, Ala, Met, Leu, Ser) (Korkmaz et al., 2010; Hajjar E et al., 2007). Preferably, the elastase 2 used in the present invention is the human enzyme, for example the protein referenced under accession number NCBI NP_001963.1. Even more preferably, the elastase 2 of the invention has the sequence SEQ ID NO: 8. The present inventors were able to demonstrate, for the first time, that the action of the neutrophil elastase 2 on human IL-33 releases the polypeptide fragment IL-33$_{aa99-270}$.

These three proteases (cathepsin G, proteinase 3 and elastase 2) form part of the family of "neutrophil serine proteases". In a specific embodiment, the cathepsin G mentioned above has the sequence SEQ ID NO: 6, the proteinase 3 has the sequence SEQ ID NO: 7, and the elastase 2 has the sequence SEQ ID NO: 8. The homologues of these proteases can also be targeted. "Homologues" here refers to the proteases having a sequence identical to at least 80%, preferably 85%, preferably 87%, preferably 90%, preferably 92%, preferably 95%, preferably 98% and even more preferably 99% of SEQ ID NO: 6, SEQ ID NO: 7 and SEQ ID NO: 8 and preserving the enzymatic activities of the corresponding elastase 2 protease, proteinase 3 and cathepsin G, as defined above.

In the sense of the present invention, the term "human interleukin 33" (IL-33) refers to a cytokine of the family IL-1. Three isoforms of IL-33 were identified in humans: these are the isoform 1 (NP_254274), the isoform 2 (NP_001186569), and the isoform 3 (NP_001186570). The IL-33 defined in the invention is the isoform 1 of IL-33, comprising 270 amino acids, and identified under accession number NP_254274. In a more specific embodiment, the IL-33 of the invention has the sequence SEQ ID NO: 1.

The term "polypeptide fragment" refers, in the present invention, to a chain of amino acids linked by peptide bonds, comprising at least 50 amino acids, preferably at least 100 amino acids and no more than 250 amino acids, preferably between around 150 amino acids and 180 amino acids, even more preferably between 160 amino acids and 175 amino acids.

The term "polypeptide fragments" as used hereinafter refers to each of the three polypeptide fragments IL-33$_{aa95-270}$, IL-33$_{aa99-270}$ and IL-33$_{aa109-270}$ as defined above.

The polypeptide fragments of the invention are biologically active, i.e. they have an in vitro and/or in vivo biological activity, for example on the activation and/or the recruitment of immune system cells.

Preferably, the polypeptide fragments of the invention have at least one (or more) improved biological activity or activities with respect to the whole form IL-33 and/or with respect to the truncated form of IL-33 already known, having the sequence SEQ ID NO: 5 (IL-33$_{aa112-270}$). This improved biological activity can be, for example, the activation and/or the recruitment of immune system cells. Thus, in a particular embodiment, each of the polypeptide fragments of the invention has an increased stimulation activity on the immune system cells with respect to the whole form of human IL-33. According to another particular embodiment, each of the polypeptide fragments of the invention has an increased recruitment activity on immune system cells with respect to the truncated form of human IL-33 having sequence SEQ ID NO: 5 (IL-33$_{aa112-270}$). Preferably, said immune system cells are the Th2 lymphocytes, mast cells, NK and iNKT killer cells, basophils and eosinophils.

The properties of stimulation of immune system cells can be evaluated in particular in vitro, for example by placing one of said fragments in contact with immune system cells and measuring their stimulation state. In this test, the immune system cells are preferably basophils or mast cells, of which the simulation state can be estimated, for example, by measuring the quantity of pro-inflammatory cytokines, such as IL-18, IL-4, IL-5, IL-6, IL-13 or GM-CSF, which they secrete (Reen D J, *Methods Mol. Biol.* 1994). The measurement of the quantity of cytokines secreted can be performed by numerous techniques well known to a person skilled in the art, and in particular by the ELISA technique. An example of such a test is presented below (cf. example b).

In a preferred embodiment, the polypeptide fragments of the invention have a better in vitro stimulation activity on the immune system cells with respect to native human interleukin 33 (hIL-33), and are capable of stimulating the secretion of at least one of these cytokines with a ratio (for example, defined as the quantity of cytokine secreted by said cells in the presence of the fragment of the invention/quantity of cytokine secreted by the same cells, in the presence of IL-33 in the whole form) preferably of at least two, and even more preferably at least three, and most preferably at least four, with respect to the whole form of human IL-33 of SEQ ID NO: 1.

It is also possible to evaluate, in vitro, the binding of these polypeptide fragments to the ST2 receptor, in order to verify that the latter is indeed stimulated by these fragments.

Moreover, the properties of recruitment of immune system cells can be evaluated in vivo, by injecting one of the peptide fragments of IL-33 into the peritoneal cavity for 6 to 7 days and by analysing the cellularity (eosinophils, neutrophils, granulocytes) in the spleen or the serum. Pathological changes can also be observed in the lungs (presence of mucous), the digestive tract (hyperplasia of epithelial cells and caliciform cells) or the plasma (increased concentration of cytokines such as IL-4, IL-5) (Schmitz J et al., *Immunity* 2005; Lüthi A. et al., *Immunity* 2009). One such example is described below (cf. example d).

In a preferred embodiment, the fragments of the invention have a better in vivo immune system cell recruitment activity than the truncated form of IL-33 having, as a sequence, amino acids 112 to 270 (SEQ ID NO: 5). More specifically, the fragments of the invention are preferably capable of inducing an increase in the weight of the spleen and/or increasing the granulocyte cellularity in the blood of mice by a factor of at least 1.8, even more preferably 2, with respect to the injection of a control vehicle (PBS), and a factor of at least 1.2, even more preferably at least 1.3 and most preferably at least 1.4, with respect to the injection of the truncated form of IL-33 of sequence SEQ ID NO: 5 (IL-33$_{aa112-270}$).

In the sense of the present invention, a biological process occurs "in vitro" when it occurs outside of an animal or a human organism, for example in a laboratory equipment (pipe, test tube, Eppendorf, etc.), therefore artificially. Preferably, this process does not involve animal or human cells. By contrast, in the sense of the present invention, a biological process occurs "in vivo" when it occurs in a human or an animal organism. In the sense of the present invention, a biological process is qualified as "ex vivo" when it involves living human or animal cells that are cultivated outside of the organism, from which they are obtained (cell line or primary cells cultivated in laboratory equipment).

In this first aspect, the present invention also relates to homologues of fragments having, as a sequence, amino acids 95 to 270 (SEQ ID NO: 2), 99 to 270 (SEQ ID NO: 3) or 109 to 270 (SEQ ID NO: 4) of human interleukin 33 (hIL-33).

The "homologues" mentioned above are polypeptide fragments that are "homologues" to those having, as a sequence, SEQ ID NO: 2, SEQ ID NO: 3 and SEQ ID NO: 4. The term "homologue" refers here to a polypeptide having a sequence identical to at least 80%, preferably 85%, preferably 87%, preferably 90%, preferably 92%, preferably 95%, preferably 97%, preferably 98% and even more preferably 99% of SEQ ID NO: 2, SEQ ID NO: 3 and SEQ ID NO: 4 and essentially having the same biological activity or activities as that or those of the corresponding polypeptide fragments.

Preferably, the "homologues" referred to in the present invention are not the fragments of human IL-33 already known, i.e. IL-33$_{1-178}$ and IL-33$_{179-270}$ of sequence SEQ ID NO: 15 and SEQ ID NO: 16 respectively, as these fragments do not have any in vitro and in vivo activity (cf. WO 2008/132709, Cayrol and Girard, *PNAS* 2009, Lüthi et al., *Immunity* 2009). Of course, the "homologues" cannot otherwise be the whole form of IL-33, having SEQ ID NO: 1, nor the artificial form of IL-33, IL-33$_{112-270}$, having SEQ ID NO: 5.

By "having essentially the same biological activity or activities" or "preserves essentially the same biological activity or activities", it is meant here that at least 90%, or even at least 95%, of at least one of the biological activities of the polypeptide fragment of SEQ ID NO: 2, SEQ ID NO: 3 or SEQ ID NO: 4 is preserved for the fragment having a sequence identical to at least 80%, preferably 85% and even more preferably 90%. Advantageously, this biological activity is the activation of immune system cells and can be measured in vitro, for example, as described above. Alternatively, this biological activity is the recruitment of immune system cells and can be measured in vivo, for example, as described above. Even more preferably, the polypeptide fragments having a sequence identical to at least 80%, preferably 85%, and even more preferably 90% of SEQ ID NO: 2, SEQ ID NO: 3 and SEQ ID NO: 4 have the same capacities for activation and recruitment of immune system cells as those of the corresponding polypeptide fragments.

"Percentage of identity" between two amino acid sequences in the terms of the present invention refers to a percentage of identical amino acid residues between the two sequences to be compared, obtained after the best alignment (optimal alignment), this percentage being purely statistical and the differences between the two sequences being distributed randomly and over their entire length. The comparisons of sequences between two amino acid sequences are traditionally performed by comparing these sequences after they have been optimally aligned, said comparison being capable of being performed by segment or by "comparison window". The optimal alignment of sequences for the comparison can be performed, aside from manually, by means of certain local homology algorithms (Smith-Waterman algorithm, Needleman-Wunsch algorithm or Lipman-Pearson algorithm), by means of computer software programs using these algorithms (GAP, BESTFIT, FASTA and TFASTA in the Wisconsin Genetics Software Package, Genetics Computer Group, 575 Science Dr., Madison, Wis., or by BLAST N or BLAST P comparison software programs).

The percentage of identity between two amino acid sequences is determined by comparing these two optimally aligned sequences, in which the amino acid sequence to be compared can comprise additions or deletions with respect to the reference sequence for an optimal alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences.

For example, it is possible to use the BLAST program "BLAST 2 sequences" (Tatusova et al., "Blast 2 sequences—a new tool for comparing protein and nucleotide sequences", *FEMS Microbiol.*, 1999) available at the site http://www.ncbi.nlm.nih.gov/gorf/bl2.html, the parameters used being those given by default (in particular for the "open gap penalty" parameters: 5, and "extension gap penalty": 2; the matrix chosen being, for example, the matrix "BLOSUM 62" proposed by the program), the percentage of identity between the two sequences to be compared being calculated directly by the program.

The phrase "amino acid sequence having at least 80%, preferably 85%, preferably 87%, preferably 90%, preferably 92%, preferably 95%, preferably 97%, preferably 98% and even more preferably 99% identity with a reference amino acid sequence" rather designates those having, with respect to the reference sequence, certain modifications, in particular a deletion, addition or substitution of at least one amino acid, a truncation or an extension, and which essentially preserve the same biological activity or activities as that or those of the corresponding peptides, are preferred. Advantageously, the activities of activation and/or recruitment of the immune system cells are essentially preserved.

In the case of a substitution of one or more consecutive or non-consecutive amino acid(s), substitutions in which the substituted amino acids are replaced by equivalent amino acids are preferred. The expression "equivalent amino acids" aims here to refer to any amino acid capable of being substituted for one of the amino acids of the base structure without, however, essentially modifying the biological activity or activities of the corresponding polypeptide fragments. Advantageously, the activity or activation and/or recruitment of the immune system cells are preserved. These equivalent amino acids can be determined either on the basis of their structural homology with the amino acids for which they are substituted, or on the basis of results of comparative biological activity tests capable of being performed between the different fragments. This search for similarities in a polypeptide sequence takes into account the preservative substitutions, which are substitutions of amino acids of the same class, such as substitution of amino acids with uncharged side chains (such as asparagine, glutamine, serine, threonine, and tyrosine), amino acids with basic side chains (such as lysine, arginine, and histidine), amino acids with acid side chains (such as aspartic acid and glutamic acid); amino acids with apolar side chains (such as glycine, alanine, valine, leucine, isoleucine, proline, phenylalanine, methionine, tryptophane, and cysteine) (Hausman R E et al. (2004). D. C: ASM Press). A person skilled in the art will easily determine the regions of the peptide fragment that can tolerate a change by reference to the Hopp/Woods and Kyte-Doolittle plots, which are well known in the field.

In a particular embodiment of the invention, the polypeptide fragments can also be modified chemically or enzymatically in order to improve their stability, their bioavailability and/or their activity. Advantageously, the activities of activation and/or recruitment of the immune system cells are improved. A person skilled in the art knows of numerous techniques for chemically or enzymatically modifying amino acids (see also David L. Nelson and Michael M. Cox, *Lehninger Principles of Biochemistry*, 3rd edition, 2000).

In a non-limiting manner, it is possible, for example, to modify one or more lysine (K) amino acids by:

amidation: this modification is simple to accomplish, the positive charge of the lysine being substituted by hydrophobic groups (for example, acetyl or phenylacetyl);

amination: by formation of secondary amides from the primary amine R=(CH2) 4-NH3+, for example by forming N-methyl, N-allyl or N-benzyl groups;

or by formation of N-oxide, N-nitroso, N-dialkyl phosphoryl, N-sulfenyl, or N-glycoside groups.

It is, moreover, also or alternatively possible to modify one or more threonine (T) and/or serine (S) amino acids of the peptides, in particular by introducing, at the OH group of the side chain of the threonine and/or the serine, an ester or ether group. Esterification, a simple operation, can be performed using a carboxylic acid, an anhydride, by bridging, etc., to form, for example, acetates or benzoates. Etherification, which produces more stable compounds, can be performed using an alcohol, a halogenide, etc., to form, for example, a methyl ether or an O-glycoside. It is, moreover, also or alternatively possible to modify one or more glutamine (Q) amino acids, for example, by amination, by forming secondary or tertiary amines, in particular with methyl, ethyl, functionalized or non-functionalized groups. It is, moreover, also or alternatively possible to modify one or more glutamate (E) and/or aspartate (D) amino acids, for example:

by esterification, to form substituted or non-substituted methyl esters, ethyl esters, benzyl esters, thiols (activated esters), etc., by amidation, in particular to form N,N dimethyl, nitroanilide, pyrrolidinyl groups, etc.

However, it is preferable not to modify the proline amino acids, which are involved in the secondary structure of the peptides, also given that the amino acids G, A and M do not generally offer possibilities for modification that would clearly be beneficial.

The fragments of the IL-33 identified by the present inventors (IL-33$_{aa95-270}$, IL-33$_{aa99-270}$ and IL-33$_{aa109-270}$, and/or their homologues), corresponding to the natural forms generated by human neutrophil proteases, can be obtained by genetic engineering, using a prokaryotic or eukaryotic recombinant protein production system, in particular by i) cultivating a microorganism or eukaryotic cells transformed by means of a nucleotide sequence coding these different fragments of IL-33 and ii) isolating the fragments of IL-33 produced by said microorganism or said eukaryotic cells. This technique is well known to a person skilled in the art. For more details concerning same, reference can be made to the following work: Recombinant DNA Technology I, Editors Ales Prokop, Raskesh K Bajpai; Annals of the New York Academy of Sciences, Volume 646, 1991. The peptide fragments of IL-33 of the invention are preferably purified/isolated from cell lysates and/or cell supernatants by which they are expressed and/or secreted. This purification can be performed by any means known to the person skilled in the art. Numerous purification techniques are described in Voet D and Voet J G, Techniques de purification des protéines et des acides nucléeiques [Protein and nucleic acid purification techniques], Chapter 6, *Biochimie*, 2nd edition.

The recombinant protein production systems use nucleotide vectors comprising nucleic acids coding the polypeptides to be synthesized, which are introduced into host cells that produce said polypeptides (for more details, refer to "Recombinant DNA Technology I", Editors Ales Prokop, Raskesh K Bajpai; Annals of the New York Academy of Sciences, Volume 646, 1991).

In a second aspect, the invention therefore relates to an isolated nucleic acid coding at least one of the polypeptide fragments according to the invention, i.e. coding at least one polypeptide having a sequence chosen from the group consisting of SEQ ID NO: 2, SEQ ID NO: 3 or SEQ ID NO: 4, or their homologues. The term "homologues" here again refers to a polypeptide having a sequence identical to at least 80%, preferably 85%, preferably 87%, preferably 90%, preferably 92%, preferably 95%, preferably 97%, preferably 98% and even more preferably 99% of one of sequences SEQ ID NO: 2, SEQ ID NO: 3 or SEQ ID NO: 4.

In a preferred embodiment, a nucleic acid according to the invention has between 486 and 528 base pairs. More preferably, a nucleic acid of the invention comprises a sequence chosen from the group consisting of SEQ ID NO: 9, SEQ ID NO: 10 or SEQ ID NO: 11.

In a third aspect, the invention also relates to a vector comprising at least one nucleic acid according to the invention. This vector can serve to produce the polypeptide fragments of the invention (cloning and/or expression vectors that contain the nucleic acid according to the invention) or to transport said fragment in vivo for gene therapy purposes.

Numerous vectors into which a nucleic acid molecule of interest can be inserted in order to introduce and maintain it in a eukaryotic or prokaryotic host cell, are known; the choice of a suitable vector is dependent on the use envisaged for this vector (for example, replication of the sequence of interest, expression of said sequence, maintenance of said sequence in extrachromosomal form or integration in the chromosomal material of the host), as well as the nature of the host cell (for example, the plasmids are preferably introduced into bacterial cells, while the YACs are preferably used in yeast). These expression vectors can be plasmids, YACs, cosmids, retroviruses, EBV-based episomes, and all vectors that a person skilled in the art may consider appropriate for the expression of said chains. In a preferred embodiment of the invention, the vector used to code the polypeptide fragment of the invention is the vector pcDNA3.1 (+) of SEQ ID NO: 14 (Invitrogen) for the in vitro studies and the pET vectors (Novagen) for large-scale productions in the bacteria.

The vectors according to the invention comprise the nucleic acid coding at least one of the polypeptide fragments of the invention, or a similar sequence, as well as the means necessary for its expression. The phrase "means necessary for the expression of a peptide", the term peptide being used for any peptide molecule, such as protein, polyprotein, polypeptide, etc., refers to any means that enables the peptide to be obtained, such as, in particular, a promoter, a transcription terminator, an origin of replication and preferably a selection marker. The means necessary for the expression of a peptide are operationally linked to the nucleic acid sequence coding for the polypeptide fragment of the invention. "Operationally linked" refers to a juxtaposition of said elements necessary for the expression of the gene coding for the polypeptide fragment of the invention, which are in a relationship that enables them to function in an expected manner. For example, there may be additional bases between the promoter and the gene coding the polypeptide fragment of the invention insofar as their functional relationship is preserved. The means necessary for the expression of a peptide can be homologous means, i.e. naturally contained in the genome of the vector used, or they can be heterologous means, i.e. added artificially from another vector and/or organism. In the latter case, said means are cloned with the polypeptide fragment to be expressed. Examples of heterologous promoters comprise (i) viral promoters such as the promoter SV40 (Simian virus 40), the promoter of the thymidine-kinase gene of the herpes simplex virus (TK-HSV-1), the LTR of the Rous sarcoma virus (RSV), the first immediate promoter of the cytomegalovirus (CMV) and the adenoviral major late promoter (MLP), as well as (ii) any cell promoter that controls the transcription of genes coding for peptides in higher eukaryotes, such as the constitutive phosphoglycerate-kinase (PGK) gene promoter (Adra et al., *Gene* 1987), the promoter of genes specific to liver alpha-antitrypsin and FIX and the SM22 promoter specific to smooth muscle cells (Moessler et al., *Development* 1996). The methods of suppression and insertion of DNA sequences in expression vectors are largely known to a person skilled in the art and consist in particular of enzymatic digestion and ligation steps. The vectors of the invention can also comprise sequences necessary for targeting peptides toward particular cellular compartments. One targeting example can be the targeting toward the endoplasmic reticulum obtained by using addressing sequences of the leader sequence type from the E3 protein of the adenovirus (Ciernik I F, et al., *The Journal of Immunology*, 1999).

The term "transcription terminator" here refers to a sequence of the genome that marks the end of the transcription of a gene or of an operon, as a messenger RNA. The transcription termination mechanism is different in prokaryotes and in eukaryotes. The person skilled in the art knows the signals to be used according to the different cell types. For example, if the cell into which the vector will be introduced is a bacterium, a Rho-independent terminator (inverted repeat sequence followed by a T series (uracils on the transcribed RNA) or a Rho-dependent terminator (consisting of a consensus sequence recognized by the Rho protein) will be used.

The term "origin of replication" (also called ori) is a single DNA sequence enabling the replication to be initiated. It is from this sequence that a one-way or two-way replication begins. The person skilled in the art knows that the structure of the origin of replication varies from one species to the other; it is therefore specific even though they all have certain characteristics. A protein complex is formed at this sequence and enables the DNA to be opened and the replication to be started.

The selection markers are well known to the skilled person. Preferably, it is a gene coding a protein conferring resistance to an antibiotic.

The vectors of the invention, comprising the nucleic acid(s) of interest of the invention, are prepared by methods commonly used by the person skilled in the art. The resulting clones can be introduced into a suitable host by standard methods known to the person skilled in the art in order to introduce polynucleotides into a host cell. Such methods comprise transformation using dextran, precipitation with calcium phosphate, transfection using polybrene, protoplast fusion, electroporation, encapsulation of polynucleotides in liposomes, biolistic injection and direct microinjection of DNA into the core. It is also possible to associate said sequence (isolated or inserted into a plasmid vector) with a substance enabling it to pass through the membrane of the host cells, such as a transporter like a nanotransporter or a liposome preparation, or cationic polymers. In addition, it is advantageously possible to combine these methods, for example by using electroporation associated with liposomes.

In a fourth aspect, the present invention relates to a microorganism or a eukaryotic host cell transformed in a transient or stable manner by—or comprising—at least one of the nucleic acids of the invention or by one of the vectors of the invention.

As examples of microorganisms suitable for the purposes of the invention, it is possible to cite yeast (Buckholz R G, Current Opinion in Biotechnology 1993) and bacteria (Olins and Lee, Current Opinion in Biotechnology 1993). As examples of eukaryotic cells, it is possible to cite cells coming from animals such as mammals (Edwards C P and Aruffo A, Current Opinion in Biotechnology 1993), reptiles, and the like. It is also possible to use plant cells. Among the mammal cells, it is possible in particular to use Chinese hamster ovary cells (CHO), monkey cells (COS and Vero cells), dwarf hamster kidney cells (BHK cells), pig kidney cells (PK 15 cells) and rabbit kidney cells (RK 13 cells), human osteosarcoma cell lines (cells 143 B), human HeLa cell lines and human hepatoma cell lines (of the Hep G2 cell type). It is also possible to use insect cells in which processes implementing baculoviruses, for example, can be implemented (Luckow V A, Journal of Virology 1993). In a preferred embodiment of the invention, the host cell used to produce the fragment of the invention is a bacterium, preferably the BL21 bacterium.

The person skilled in the art knows the conditions in which to cultivate these cells, as well as the experimental conditions necessary for the expression of the polypeptide fragments by these cells.

In another aspect, the invention also relates to a process for producing a recombinant polypeptide fragment according to the invention, characterized in that it comprises the following steps:

a) culturing, in a suitable culture medium and under suitable culture conditions, of a host cell according to the invention; and b) isolating the polypeptide fragment according to the invention produced in step a.

The fragment can be isolated (purified) from the cell expressing said fragment. In this case, a preliminary step of lysis of said cells may be necessary.

The culture media and conditions associated with each cell type used for the production of recombinant proteins are well known to the person skilled in the art.

The isolation (or the purification) of the polypeptide fragment of the invention can be performed by any means known to the person skilled in the art. It is possible to cite, for example, differential precipitation or ultracentrifugation. It may also be advantageous to purify the fragments of interest by ion exchange chromatography, affinity chromatography, molecular sieving or isofocusing. All of these techniques are described in Voet D and Voet J G, Techniques de purification des proteines et des acides nucléiques [Nucleic acid and protein purification techniques], Chapter 6, Biochimie, 2nd edition.

More specifically, in a first step, the material from which the protein is to be extracted (animal tissue, plant part, bacteria, etc.) is generally ground. Various equipment ("Waring Blender", Potter-Eveljhem apparatus, "Polytron", etc.) can be used for this purpose. This homogenization is performed in a buffer of suitable composition, well known to the person skilled in the art. The homogenate thus obtained is then clarified, usually by centrifugation, to remove the poorly ground large particles or to obtain the cell fraction containing the protein sought. If the protein happens to be in a cellular compartment, a gentle detergent (Triton, Tween, etc., sometimes deoxycholate) is generally used to release it by dissolving the membranes of said compartment. The use of detergent must often be performed in a controlled manner because detergents can break the lysosomes, thereby releasing hydrolytic enzymes (proteases, nucleases, etc.), which can attack and destroy the proteins or other molecules to be isolated. Special precautions must be taken when working with proteins sensitive to degradation or in a small number. A common solution to this problem is the inclusion in the solutions of protease inhibitors that are either physiological (inhibitor of trypsin antipain, leupeptin, etc.) or artificial (E64, PMSF, etc.). Then, there are various techniques for isolating the protein sought. One of the methods that is best for large volumes is differential precipitation with ammonium sulfate. Ion exchange chromatography or affinity chromatography, applicable to large sample volumes but having a relatively good separation power, are good intermediate methods. To finalize the purification, molecular sieving or isofocusing are often used. These techniques make it possible to refine the purity, but require very small volumes of concentrated proteins. It is often advantageous, between these steps, to remove the salts or products used in these chromatography operations. This can be obtained by dialysis or by ultrafiltration.

It may be advantageous to use a vector according to the invention having a sequence enabling the polypeptide fragments of the invention to be identified. In addition, it may be advantageous to facilitate secretion in a prokaryotic or eukaryotic system. Indeed, in this case, the recombinant fragments of interest will be present in the supernatant of the cell culture rather than inside the host cells.

Thus, by using one or the other of these techniques, and by contrast with the whole form of human IL-33, the polypeptide fragments of IL-33 identified by the present inventors (IL-33$_{aa95-270}$, IL-33$_{aa99-270}$ and IL-33$_{aa109-270}$) can be produced by the recombinant cells of the invention in large quantities (cf. example c) above). More specifically, the fragments of the invention can be produced at levels reaching at least 1 mg per liter, preferably 2 mg per liter, and even more preferably, 5 mg per liter of cell culture.

Alternatively, it is possible to prepare the polypeptide fragments according to the invention by chemical synthesis. Such a preparation process is also an objective of the invention. The person skilled in the art knows the chemical synthesis processes, for example, the techniques implementing solid phases or techniques using partial solid phases, by condensation of fragments or by a classic synthesis in solution. The fragments of the invention can, for example, be synthesized by synthetic chemistry techniques, such as Merrifield-type synthesis, which is advantageous for reasons of purity, antigenic specificity, absence of undesired secondary products and ease of production. This chemical synthesis can be coupled with a genetic engineering approach or genetic engineering alone using techniques well known to a person skilled in the art and described, for example, in Sambrook J. et al., Molecular Cloning: A Laboratory Manual, 1989. The reagents and starting products are commercially available or can be synthesized by well-known conventional techniques (see, for example, WO 00/12508, WO 2005/085260).

The new IL-33 fragments identified by the present inventors have, in vitro and in vivo, a biological activity superior to that of the whole form of human IL-33 and/or the truncated form IL-33$_{aa112-270}$ used until now.

These fragments can advantageously be used as in vitro agonists of the ST2 receptors or of any other receptor binding to human IL-33. In another aspect, the invention also relates to the fragments of the invention for their use as in vivo agonists of the ST2 receptors or of any other receptor binding to human IL-33. "ST2 receptor" preferably refers to the protein of sequence SEQ ID NO: 12 (isoform 1, NP_057316.3) or SEQ ID NO: 13 (isoform 2, NP_003847.2), also referred to as "T1", "DER4", "IL1R1", "FIT-1", "MGC32623" or "IL33R".

The fragments of the invention are capable of effectively stimulating the secretion of IL-6 by in vitro mast cells, and of recruiting, in vivo, the immune system cells (increase in the spleen weight and the number of granulocytes in the blood of mice). They can therefore have, in vivo, a significant therapeutic activity, in particular against diseases reacting positively to the administration of native human IL-33.

In another aspect, the present invention therefore relates to a pharmaceutical composition comprising at least one of the isolated polypeptide fragments of the invention, or at least one of the nucleic acids coding the polypeptide fragments of the invention. If the composition comprises the polypeptide fragment of the invention, said fragment can be obtained by recombinant means or by chemical synthesis means.

Preferably, a pharmaceutically acceptable excipient and/or vehicle will be added to said composition. In the present description, "pharmaceutically acceptable vehicle" refers to a compound or a combination of compounds involved in a pharmaceutical composition that do not cause secondary reactions and that enable, for example, the administration of the active compound(s) to be facilitated, its lifetime and/or efficacy in the organism to be increased, its solubility in solution to be increased, or its preservation to be improved. These pharmaceutically acceptable vehicles are well known and will be adapted by a person skilled in the art according to the nature and mode of administration of the active compound(s) chosen.

Preferably, these compounds will be administered systemically, in particular by the intravenous, intramuscular, intradermal, intraperitoneal or subcutaneous, oral or topical route (by means of gels, aerosols, drops, etc.). More preferably, the pharmaceutical composition of the invention will be administered several times, spread out over time. Its mode of administration, dosage and optimal galenic form can be determined according to criteria generally taken into account in the establishment of a treatment suitable for a patient, such as, for example, the age or the body weight of the patient, the seriousness of his or her general state, tolerance to the treatment and secondary effects observed.

In another aspect, the invention also relates to the polypeptide fragments of the invention, for their use as a drug.

More specifically, the invention relates to each of the polypeptide fragments of the invention, for their use as a drug making it possible to treat diseases that react positively to the administration of native human IL-33, such as, for example, infectious diseases such as sepsis, *Pseudomonas keratitis*, tuberculosis or infections due to a nematode or to the influenza virus, atherosclerosis, cardiovascular diseases such as myocardial infarction, cancer or adipose tissue inflammation in obesity. In other words, the invention relates to the use of at least one of the polypeptide fragments of the invention, for the production of a drug intended to treat infectious diseases such as sepsis, *Pseudomonas keratitis*, tuberculosis or infections due to a nematode or to the influenza virus, atherosclerosis, cardiovascular diseases such as myocardial infarction, cancer or adipose tissue inflammation in obesity.

The cardiovascular diseases concerned by the present invention are, for example, coronary diseases, cardiac muscle diseases, cardiac valve diseases, pericardial disease, cardiac rhythm or conduction diseases, vessel diseases or others. The coronary diseases concerned are, for example, angina pectoris or myocardial infarction. The cardiac muscle diseases concerned by the invention are, for example, cardiomyopathy or heart failure. The cardiac valve diseases concerned are, for example, endocarditis or cardiac valve diseases. "Pericardial disease" commonly refers to pericarditis. The cardiac rhythm or conduction diseases are, for example, cardiovascular syncope, cardiac conduction disorders or cardiac rhythm disorders. The vessel diseases concerned are, for example, aneurism, lower limb arteriopathy obliterans, acute aortic dissection, pulmonary arterial hypertension, or thromboembolic disease. The other diseases concerned by the invention are, for example, cardiocirculatory arrest, congenital cardiopathy, arterial hypertension, arterial hypotension, or Adams-Stokes syndrome.

Among the cancers that can be prevented and/or treated by the polypeptide fragment(s) of the invention are, in particular, prostate cancer, osteosarcoma, lung cancer, breast cancer, endometrial cancer, colon cancer, multiple myeloma or ovarian cancer, pancreatic cancer, melanoma or any other cancer.

The present invention is also directed at a treatment method comprising the administration to a patient of a pharmaceutical composition comprising an effective quantity of one of the polypeptide fragments of the invention or one of the nucleic acids of the invention coding for same. Preferably, this treatment method makes it possible to prevent and/or treat infectious diseases such as sepsis, *Pseudomonas keratitis*, tuberculosis or infections due to a nematode or to the influenza virus, atherosclerosis, cardiovascular diseases, cancer or adipose tissue inflammation in obesity, in patients suffering there from.

The present invention therefore relates in particular to a pharmaceutical composition comprising the nucleic acid of the invention or the nucleotide vector of the invention. This pharmaceutical composition can therefore be used for gene therapy purposes.

To this end, the present invention also relates to mammal cells, including human cells, preferably non-embryonic, comprising one of the vectors or one of the nucleic acids of the invention. In the context of the present invention, the principle of gene therapy is to administer to a patient a nucleic acid that codes the polypeptide fragment(s) of interest of the invention, under conditions so that they are expressed in vivo by the cells of the patient in whom the nucleic acid has been transferred.

Such a nucleic acid can in particular be in the form of a DNA vector, for example, a plasmid vector. It is possible to administer one or more vectors, each vector being capable of having one or more sequence(s) coding for at least one of the polypeptide fragments of interest. The DNA vector(s) can be introduced in vivo by any technique known to the person skilled in the art. In particular, it is possible to introduce the DNA vector in vivo in naked form, i.e. without the assistance of any vehicle or system that would facilitate the transfection of the vector into the cells (EP 465 529). A "gene gun" can also be used, for example by depositing the DNA at the surface of "gold" particles and by projecting them so that the DNA penetrates the skin of a patient. Injections by means of a liquid gel are also possible for transfecting at the same time skin, muscle, fat tissue and mammary tissue (Furth et al., *Anal Biochem* 1992). Techniques of microinjection, electroporation, precipitation with calcium phosphate, formulations using nanocapsules or liposomes are other available techniques. Biodegradable polyalkyl cyanoacrylate nanoparticles are particularly advantageous. In the case of liposomes, the use of cationic lipids promotes the encapsulation of the nucleic acids that are negatively charged, and facilitates fusion with the negatively charged cell membranes. Alternatively, the vector can be in the form of a recombinant virus comprising, inserted in its genome, a nucleic acid sequence that codes for said peptide(s). The viral vector can preferably be chosen from an adenovirus, a retrovirus, in particular a lentivirus, as well as an adeno-associated virus (AAV), a herpes virus, a cytomegalovirus (CMV), a vaccine virus, etc. Advantageously, the recombinant virus is a defective virus.

The term "defective virus" refers to a virus incapable of replicating in a target cell. Generally, the genome of defective viruses is deprived of at least the sequences necessary for the replication of said virus in the infected cell. These regions can be eliminated, made non-functional or be substituted by other sequences and in particular by the nucleic acid that codes for the polypeptide fragment of interest. Nevertheless, preferably, the defective virus preserves, in spite of it all, the sequences of its genome necessary for the encapsulation of viral particles. A targeted administration of genes is, for example, described in the application WO 95/28 494.

In another aspect, the present invention relates to the use of a polypeptide fragment according to the invention, optionally obtained by one of the methods of the invention, or the nucleic acid of the invention, in combination with another drug, for example in combination with a chemotherapeutic agent for the treatment of cancer, associated with a vascular prosthesis (or stent) for the angioplasty treatment of cardiovascular diseases, or as an adjuvant of a vaccine against a virus, such as the influenza virus.

In a preferred embodiment, the polypeptide fragment of the invention is combined with a chemotherapeutic agent comprised in the group consisting of: alkylating agents, antimetabolites, plant alkaloids, topoisomerase inhibitors, antitumor antibiotics, or mitotic spindle poisons. "Alkylating agents" refer, among others, to busulfan, carboplatin, chlorambucil, cisplatin, cyclophosphamide, isosfamide, melphalan, mechlorethamine, oxaliplatin, uramustin, or even temozolomide. "Antimetabolites" refer, among others, to azathioprine, capecitabine, cytarabine, floxuridine, fludarabine, fluorouracil, gemcitabine, methotrexate, or even pemetrexed. The "plant alkaloids" are, for example, vinblastine and vincristine. The "topoisomeriase inhibitors" are, for example, irinotecan, topotecan, or etoposide. The "antitumor antibiotics" are, for example, bleomycin, daunorubicin, doxorubicin, epirubicin, hydroxyurea, idarubicin, mitomycin C, or mitoxantrone. Finally, the "mitotic spindle poisons" are, for example docetaxel, paclitaxel, vinblastine, vincristine, or vinorelbine.

According to another aspect, the present invention relates to the use of an isolated polypeptide fragment according to the invention, optionally obtained by one of the methods of the invention, or the nucleic acid of the invention, for diagnosing an infection or trauma in an individual.

The diagnosis could be established by using an ELISA technique making it possible to detect specifically the new fragments of IL-33 (IL-33$_{aa95-270}$, IL-33$_{aa99-270}$ and IL-33$_{aa109-270}$) in the serum or the plasma of patients.

Indeed, an increase in the quantity of IL-33 in the blood or the serum could indicate an infection, an inflammation or trauma in an individual. It is therefore possible to envisage using the polypeptide fragments of the invention that are capable of being formed in vivo by the action of the endogenous proteases, as a marker of an infectious or inflammatory state.

Advantageously, these particular IL-33 fragments can be detected by means of antibodies specifically recognizing them.

In a final aspect, the present invention therefore relates to a monoclonal antibody specifically recognizing one of the polypeptide fragments of the present invention, but not recognizing the whole form IL-33$_{aa1-270}$ or the truncated form IL-33$_{aa112-270}$. Advantageously, said antibody is a conformational antibody, i.e. an antibody recognizing a conformational epitope.

An antibody according to the invention can be prepared by the classic techniques known to the person skilled in the art, such as those described in Antibodies: A Laboratory Manual, E. Howell and D Lane, Cold Spring Harbor Laboratory, 1988.

More specifically, such an antibody can be produced from hybridomas obtained by fusion of B lymphocytes of an animal immunized by one or more of the polypeptide fragments of the invention, with myelomas, according to the technique of Köhler and Milstein (Nature, 1975); the hybridomas are cultivated in vitro, in particular in fermenters, or produced in vivo, in the form of ascites; alternatively, said monoclonal antibody can be produced by genetic engineering as described in the U.S. Pat. No. 4,816,567.

The antibodies according to the invention that specifically recognize the polypeptide fragments of the invention with a high affinity (affinity constant to the order of the nM), represent reliable and sensitive diagnostic reagents for the detection, using a suitable biological sample (whole blood, mononucleated cells of the peripheral blood, tumour biopsy), of patients with latent infections or trauma.

In a particular embodiment, the present invention therefore also relates to a method for diagnosing infections or trauma using the antibodies of the invention. This diagnostic method can use these antibodies in flow cytometry, immunocytochemistry or immunohistochemistry or immunoprecipitation using non-fixed cells (frozen or living) or fixed cells under non-denaturing conditions that are known to a person skilled in the art.

The invention will be described more specifically in the examples below.

EXAMPLES a) Demonstration of IL-33 Fragments of the Invention

Whole human IL-33 proteins (IL-33$_{1-270}$, SEQ ID NO: 1) or truncated human IL-33 proteins (IL-33$_{112-270}$, SEQ ID NO: 5) were produced in vitro according to the classic techniques of protein production in reticulocyte lysates according to the manufacturer's recommendations (Promega TnT Coupled Reticulocyte Lysate Systems ref L4610): 1 µg of plasmid enabling the expression of full-size or truncated IL-33 (pcDNA3-IL33 1-270 or 95-270 or 99-270 or 109-270) is mixed with the rabbit reticulocyte lysate (25 µl) containing the reaction buffer 10× (2 µl), the polymerase T7 (1 µl), the amino acid mixture 1 mM (1 µl), the RNase inhibitor RNAsin (40 U/µl) in a final reaction volume of 50 µl. A control is produced using the empty vector pcDNA3. Incubation is performed at 30° C. for around 90 min. For the cleavage by the neutrophil proteases, 5 µl of lysate, programmed or not, are then incubated at 37° C. for 1 hour with 1 mU of cathepsin G (Calbiochem, ref: 219373), or 30 min with 0.3 U of elastase (Calbiochem ref: 324681) or 30 min with 0.25 µg of PR3 (Calbiochem ref: 539483). The cleavage products are analysed by SDS-PAGE and Western Blot gel using a monoclonal antibody directed against the C-terminal portion of IL-(IL-33305B, Alexis Biochemical ref: ALX-804-726) (FIG. 2A). Human IL-33 is the target of the recombinant proteases Cathepsin G (Cat G), Elastase 2 (Elastase), and Proteinase 3 (PR3), which generate, in vitro, the three mature fragments IL-33$_{aa95-270}$, IL-33$_{aa99-270}$ and IL-33$_{aa109-270}$. However, the three neutrophil proteases do not cleave the IL-1 cytokine-type domain (C-terminal domain), as shown in the two blots at the bottom of FIG. 2A.

In addition, human neutrophils were isolated and purified from human fresh whole blood collected on an EDTA tube, using the Polymorphprep separation medium (Axis-Shield; ref 1114683). The neutrophils are resuspended in RPMI/Hepes (25 mM) and distributed in 96-well plates in an amount of 100,000 neutrophils/ml and 100 μl/wells, then activated with PMA (Phorbol 12 myristate acetate 13, 25 nM) for 2 hours at 37° C. The whole IL-33 protein (25 μl of programmed lysate as described above) was incubated with these human neutrophils, in the presence or in the absence of a serine protease inhibitor (AEBSF, 5 mM). The analysis of the generated fragments was performed by Western Blot using an anti-IL-33 antibody directed against the C-terminal portion (IL-33305B; Alexis Biochemical, ref: ALX-804-726). A comparison of the sizes of the generated fragments was performed using the recombinant proteins IL-33$_{aa95-270}$, IL-33$_{aa99-270}$ and IL-33$_{aa109-270}$. The results obtained are shown in FIG. 2B. They show that human IL-33 is actually the target ex vivo of the human neutrophil proteases Cathepsin (Cat G), Elastase 2 (Elastase), and Proteinase 3 (PR3).

b) The New Fragments of IL-33 are "Superactive" In Vitro

The biological activity of the new IL-33 fragments IL-33$_{aa95-270}$, IL-33$_{aa99-270}$ IL-33$_{aa109-270}$ was tested in vitro in two functional tests, one based on the secretion of ST2-dependent IL-5 in a human basophil line, and the other based on the secretion of ST2-dependent IL-6 in a murine mast cell line.

Briefly, MC/9 mast cells (ATCC CRL-8306) are kept in the DMEM medium (ATCC, Ref: 30-2002) containing 6 mM of glutamine, 0.05 mM of 2-mercaptoethanol, 10% Rat-T-STIM (Beckton-Dickinson, ref: 354115) and 10% foetal calf serum (ATCC, ref: 30-2020). 200,000 cells per well are distributed in 96-well plates in an amount of 200 μl/well, then incubated for 24 hours at 37° C. with the proteins IL-33$_{aa1-270}$, IL-33$_{aa95-270}$, IL-33$_{aa99-270}$ and IL-33$_{aa109-270}$ (10 μl of programmed reticulocyte lysate). The quantity of IL-6 secreted in the culture supernatant was measured classically by the ELISA technique using the "mouse IL-6" kit (R&D, ref: 406). The results were brought to the value obtained for the full-size IL-33 IL-33$_{aa1-270}$.

The human basophil cells KU812 (ATCC CRL-2099) are kept in the RPMI 1640 medium (ATCC, Ref: 30-2001) supplemented with 10% foetal calf serum (ATCC, ref: 30-2020). $10^6$ cells per well are distributed in 96-well plates in an amount of 200 μl/well, then incubated for 24 hours at 37° C. with the proteins IL-33$_{aa1-270}$, IL-33$_{aa95-270}$, IL-33$_{aa99-270}$ and IL-33$_{aa109-270}$ (8 μl of programmed reticulocyte lysate). The quantity of IL-5 secreted in the culture supernatant was measured classically owing to the ELISA technique with the "human IL-5" kit (R&D, ref: DY205).

In each of these tests, it was demonstrated that the recombinant proteins IL-33$_{aa95-270}$, IL-33$_{aa99-270}$ and IL-33$_{aa109-270}$ had a greater activity than that of the full-size active form IL-33$_{aa1-270}$ (FIGS. 3B and 3C). The new IL-33 fragments IL-33$_{aa95-270}$ IL-33$_{aa99-270}$ and IL-33$_{aa109-270}$ are therefore "superactive" with respect to the whole form in vitro.

c) Process for Producing/Purifying IL-33 Fragments of the Invention by Recombinant Means The whole or truncated human recombinant IL-33 proteins were produced in bacteria in fusion with an N-terminal 6× Histidine tag so as to enable the purification of proteins, according to the classic techniques used by a person skilled in the art. The Histidine Tag was then removed by cleavage with thrombin and the protein of interest was purified by steric exclusion chromatography.

Briefly, a liter of culture medium is seeded with the transformed strain (BL21 pLysS-pET15b-IL-33$_{aa1-270}$ or BL21 pLysS-pET15b-IL-33$_{aa95-270}$, or BL21 pLysS-pET15b-IL-33$_{aa99-270}$ or BL21 pLysS-pET15b-IL-33$_{aa109-270}$). When the DO reaches 0.7, the expression of the protein of interest is induced by the addition of 1 mM of IPTG for 4 hours at 37° C. The bacteria are centrifuged and the pellet is contacted with the lysis buffer (Na$_2$HPO$_4$ 50 mM, NaCl 300 mM, Imidazole 20 mM, Triton 0.5%, Dnase I 1 mM, lysozyme 1 mM, protease inhibitor). After sonication and ultracentrifugation, the bacterial lysate is collected and incubated with Nickel-NTA beads at 4° for 4 hours. The beads are washed and the protein purified by affinity is eluted with 500 mM of imidazole. The eluate is then separated from the imidazole and dialyzed in a Tris-NaCl buffer by centrifugation/concentration using the Vivaspin (Sartorius; 20 mL of threshold 10 kDa). The histidine tag is cleaved by the thrombin (250 units/mL, 4° C., 20 hours) and the protein is then purified by gel permeation chromatography ("Gel Filtration"—Superdex 75 column) followed by concentration by Vivaspin (Sartorius). The analysis of the different purification steps is performed by SDS-PAGE gel and Coomassie blue stain. The purified proteins are quantified by Nanodrop assay (Thermoscientific), and the presence of endotoxin was determined using the "*Limulus Amebocyte* Lysate" kit (Cambrex, Ref: 50-647U).

Examples of the production/purification of IL-33 proteins (whole or cleaved forms) are shown in FIG. 4. At least 9 mg of proteins corresponding to the fragments of IL-33 (IL-33$_{95-270}$, IL-33$_{99-270}$, IL-33$_{109-270}$) could be produced from a liter of bacterial culture, while less than 1 μg could be obtained for the full-size form. The yield for the production of IL-33 fragments is therefore at least 9000 times greater than that obtained for the full-size form 1-270.

d) The New IL-33 Fragments are Biologically "Superactive" In Vivo

The biological activity of the new IL-33 fragments was tested in vivo in the mouse and compared with the activity of the artificial form IL-33$_{aa112-270}$. The use of the whole human protein IL-33 in this experiment is excluded since it is impossible to obtain the required quantity of protein for the injection (>340 μg, taking into account the number of mice to be injected, and the total number of injections to be performed). The recombinant proteins IL-33$_{aa112-270}$, IL-33$_{aa95-270}$, IL-33$_{aa99-270}$ and IL-33$_{109-270}$ produced in *Escherichia coli* (vector pET15b, Novagen; bacteria BL21) and purified by affinity chromatography were injected by the intraperitoneal route (4 μg in 200 μl PBS) in Balb/C mice (12 female mice from 8 to 10 weeks) for 7 days, daily. The analysis of the mice showed clear pathological changes, in particular with an increase in the volume and weight of the spleen after 7 days (FIG. 4A), and hyperplasia of the caliciform cells of the jejunum (FIG. 4B). Interestingly, two of the new IL-33 fragments (IL-33$_{aa95-270}$ and IL-33$_{aa99-270}$) induce an increase in the number of granulocytes (predominantly neutrophils) in the blood of the mice after 7 days, an increase that is significantly higher than that induced by the truncated form IL-33$_{aa112-270}$ (FIG. 4C), indicating that the new fragments of IL-33, IL-33$_{aa95-270}$ and IL-33$_{aa99-270}$, are "superactive" in vivo. This last result is entirely unexpected because the existence of IL-33 fragments that are more active than the form IL-33$_{aa112-270}$ was never suspected before.

BIBLIOGRAPHIC REFERENCES

Adra et al., 1987, *Gene*, 60:65-74
Ali et al., *Biochem Biophys Res Commun* 2010, 391:1512-6
Alves-Filho et al., *Nature Medicine* 2010, 16:708-12
Baekkevold E et al., *American Journal Pathology* 2003, 163:69-79
Bieth J G, *J. Soc. Biol.* 2001, 195(2):173-9
Buckholz R G, *Current Opinion in Biotechnology* 1993, 4(5):538-42
Burster T et al., *Molecular Immunology* 2010, 47:658-665
Carriere V et al., *PNAS* 2007, 104:282-287
Cayrol and Girard, *PNAS* 2009, 106(22):9021-6
Chackerian A A et al., *Journal of Immunology* 2007, 179: 2551-5
Ciernik I F et al., *The Journal of Immunology*, 1999, 162, 3915-3925
David L. Nelson and Michael M. Cox, *Lehninger Principles of Biochemistry*, 3rd edition, 2000
Edwards C P and Aruffo A, *Current Opinion in Biotechnology* 1993, 4(5):558-63
Furth P A et al., 1992 *Anal Biochem.* 1992 September; 205(2):365-8
Hausman R E et al. (2004). *The cell: a molecular approach*. Washington, D.C.: ASM Press, p. 51
Hajjar E et al., *FEBS Letters* 2007, 581:5685-5690.
Hazlett et al., *Invest Ophtalmol Vis Sci* 2010, 51:1524-32
Humphreys et al., *Journal of Immunology* 2008, 180:2443-9
Kargi et al., 1990, *J. Histochem. Cytochem.* 38(8):1179-86
Köhler and Milstein, *Nature*, 1975, 256, 495-497.
Korkmaz B. et al., *Pharmacological Reviews* 2010, 62:726-759.
Liew et al., *Nature Rev Immunology* 2010, 10:103-110
Lingel et al., *Structure* 2009, 17:1398-410
Luckow V A, *Journal of Virology* 1993, 67(8) 4566-79
Lüthi et al., *Immunity* 2009; 31:84-98
Miller et al., *J. Exp. Med.* 2008, 205:339-46
Miller et al., *Circ Res* 2010 107:650-8
Moessler et al., *Development* 1996, 122: 2415-2425.
Moussion et al., *PLoS ONE* 2008, 3(10):e3331
Nufer O et al., *Biochemistry* 1999, 38(2):636-42
Olins and Lee, *Current Opinion in Biotechnology* 1993, 4(5):520-5
Pushparaj et al., *PNAS* 2008, 106:9773-8
Rankin et al., *J Immunol* 2010, 184:1526-35.
Rao N V et al., *PNAS* 1991, 88; 9253-9256
Reen D J, *Methods Mol. Biol.* 1994, 32:461-6.
Sambrano G R et al., *J. Biol. Chem.* 2000, 275:6819-6823.
Schmitz et al., *Immunity* 2005, 23:479-90
Seki et al., *Circ Heart Fail* 2009, 2:684-91
Sims J E and Smith D E, *Nature Rev Immunology* 2010, 10:89-102
Stolarski et al., *Journal of Immunology* 2010, 185:3472-80
Talabot-Ayer et al., *J. Biol. Chem.* 2009; 284:19420-6
Tatusova et al., *FEMS Microbiol.*, 1999 Lett. 174:247-250
Xu et al., *Journal of Immunology* 2010; 184:2620-6

---

The invention claimed is:

1. A method for increasing granulocyte number in a patient having sepsis or cancer comprising administering to the patient an effective amount of one or more human interleukin 33 (hIL-33) polypeptide fragment consisting of a sequence selected from the group consisting of amino acids 95 to 270 (SEQ ID NO: 2), 99 to 270 (SEQ ID NO: 3), and 109 to 270 (SEQ ID NO: 4), wherein the effective amount of said fragment induces an increase in granulocyte number in the blood of the patient.

2. The method of claim 1, wherein the human interleukin 33 (hIL-33) polypeptide fragment is a product of hIL-33 cleavage by a protease of human neutrophils selected from the group consisting of: cathepsin G (EC 3.4.21.20), leukocyte proteinase 3 (EC 3.4.21.76), and neutrophil elastase 2 (EC 3.4.21.37).

3. The method of claim 1, wherein the polypeptide fragment induces a level of granulocytes in blood higher than the level of granulocytes in blood induced by the same amount of human interleukin 33 (hIL-33) fragment consisting of amino acid sequence 112 to 270 of hIL-33 (SEQ ID NO: 5).

4. The method of claim 1, wherein the polypeptide fragment is administered in the form of a pharmaceutical composition comprising a pharmaceutically acceptable excipient.

5. A method for increasing granulocyte number in a patient having sepsis or cancer comprising administering to the patient having sepsis or cancer one or more isolated human interleukin 33 (hIL-33) polypeptide fragment, said fragment consisting of a sequence selected from the group consisting of amino acids 95 to 270 (SEQ ID NO: 2), 99 to 270 (SEQ ID NO: 3), and 109 to 270 (SEQ ID NO: 4) wherein said fragment is a product of hIL-33 cleavage with at least one protease of human neutrophils selected from the group consisting of: cathepsin G (EC 3.4.21.20), leukocyte proteinase 3 (EC 3.4.21.76), and neutrophil elastase 2 (EC 3.4.21.37), wherein the fragment is administered to the subject in an amount sufficient to increase the number of granulocytes in the patient's blood.

6. The method of claim 5, wherein the polypeptide fragment induces a level of granulocytes in blood that is higher than the level of granulocytes in blood induced by the same amount of a human interleukin 33 (hIL-33) fragment consisting of amino acid sequence 112 to 270 of hIL-33 (SEQ ID NO: 5).

7. The method of claim 5, wherein the polypeptide fragment is administered in the form of a pharmaceutical composition comprising a pharmaceutically acceptable excipient.

* * * * *

SEQUENCE LISTING

```
<160> NUMBER OF SEQ ID NOS: 16

<210> SEQ ID NO 1
<211> LENGTH: 270
<212> TYPE: PRT
<213> ORGANISM: homo sapiens

<400> SEQUENCE: 1

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
```

```
                130                 135                 140
Ile Tyr Val Glu Asp Leu Lys Lys Asp Glu Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
                260                 265                 270

<210> SEQ ID NO 2
<211> LENGTH: 176
<212> TYPE: PRT
<213> ORGANISM: homo sapiens

<400> SEQUENCE: 2

Ala Phe Gly Ile Ser Gly Val Gln Lys Tyr Thr Arg Ala Leu His Asp
1               5                   10                  15

Ser Ser Ile Thr Gly Ile Ser Pro Ile Thr Glu Tyr Leu Ala Ser Leu
                20                  25                  30

Ser Thr Tyr Asn Asp Gln Ser Ile Thr Phe Ala Leu Glu Asp Glu Ser
            35                  40                  45

Tyr Glu Ile Tyr Val Glu Asp Leu Lys Lys Asp Glu Lys Lys Asp Lys
50                  55                  60

Val Leu Leu Ser Tyr Tyr Glu Ser Gln His Pro Ser Asn Glu Ser Gly
65                  70                  75                  80

Asp Gly Val Asp Gly Lys Met Leu Met Val Thr Leu Ser Pro Thr Lys
                85                  90                  95

Asp Phe Trp Leu His Ala Asn Asn Lys Glu His Ser Val Glu Leu His
            100                 105                 110

Lys Cys Glu Lys Pro Leu Pro Asp Gln Ala Phe Phe Val Leu His Asn
        115                 120                 125

Met His Ser Asn Cys Val Ser Phe Glu Cys Lys Thr Asp Pro Gly Val
    130                 135                 140

Phe Ile Gly Val Lys Asp Asn His Leu Ala Leu Ile Lys Val Asp Ser
145                 150                 155                 160

Ser Glu Asn Leu Cys Thr Glu Asn Ile Leu Phe Lys Leu Ser Glu Thr
                165                 170                 175

<210> SEQ ID NO 3
<211> LENGTH: 172
<212> TYPE: PRT
<213> ORGANISM: homo sapiens

<400> SEQUENCE: 3

Ser Gly Val Gln Lys Tyr Thr Arg Ala Leu His Asp Ser Ser Ile Thr
1               5                   10                  15

Gly Ile Ser Pro Ile Thr Glu Tyr Leu Ala Ser Leu Ser Thr Tyr Asn
```

```
                    20                  25                  30
Asp Gln Ser Ile Thr Phe Ala Leu Glu Asp Glu Ser Tyr Glu Ile Tyr
            35                  40                  45

Val Glu Asp Leu Lys Lys Asp Glu Lys Lys Asp Lys Val Leu Leu Ser
 50                  55                  60

Tyr Tyr Glu Ser Gln His Pro Ser Asn Glu Ser Gly Asp Gly Val Asp
 65                  70                  75                  80

Gly Lys Met Leu Met Val Thr Leu Ser Pro Thr Lys Asp Phe Trp Leu
                85                  90                  95

His Ala Asn Asn Lys Glu His Ser Val Glu Leu His Lys Cys Glu Lys
            100                 105                 110

Pro Leu Pro Asp Gln Ala Phe Phe Val Leu His Asn Met His Ser Asn
            115                 120                 125

Cys Val Ser Phe Glu Cys Lys Thr Asp Pro Gly Val Phe Ile Gly Val
            130                 135                 140

Lys Asp Asn His Leu Ala Leu Ile Lys Val Asp Ser Ser Glu Asn Leu
145                 150                 155                 160

Cys Thr Glu Asn Ile Leu Phe Lys Leu Ser Glu Thr
            165                 170

<210> SEQ ID NO 4
<211> LENGTH: 162
<212> TYPE: PRT
<213> ORGANISM: homo sapiens

<400> SEQUENCE: 4

His Asp Ser Ser Ile Thr Gly Ile Ser Pro Ile Thr Glu Tyr Leu Ala
 1               5                  10                  15

Ser Leu Ser Thr Tyr Asn Asp Gln Ser Ile Thr Phe Ala Leu Glu Asp
                20                  25                  30

Glu Ser Tyr Glu Ile Tyr Val Glu Asp Leu Lys Lys Asp Glu Lys Lys
            35                  40                  45

Asp Lys Val Leu Leu Ser Tyr Tyr Glu Ser Gln His Pro Ser Asn Glu
 50                  55                  60

Ser Gly Asp Gly Val Asp Gly Lys Met Leu Met Val Thr Leu Ser Pro
 65                  70                  75                  80

Thr Lys Asp Phe Trp Leu His Ala Asn Asn Lys Glu His Ser Val Glu
                85                  90                  95

Leu His Lys Cys Glu Lys Pro Leu Pro Asp Gln Ala Phe Phe Val Leu
            100                 105                 110

His Asn Met His Ser Asn Cys Val Ser Phe Glu Cys Lys Thr Asp Pro
            115                 120                 125

Gly Val Phe Ile Gly Val Lys Asp Asn His Leu Ala Leu Ile Lys Val
            130                 135                 140

Asp Ser Ser Glu Asn Leu Cys Thr Glu Asn Ile Leu Phe Lys Leu Ser
145                 150                 155                 160

Glu Thr

<210> SEQ ID NO 5
<211> LENGTH: 159
<212> TYPE: PRT
<213> ORGANISM: Artificial Sequence
<220> FEATURE:
<223> OTHER INFORMATION: Truncated form of human IL-33 humaine Hs IL33
      amino acids 112-270

<400> SEQUENCE: 5
```

```
Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Asp Lys Val
        35                  40                  45

Leu Leu Ser Tyr Tyr Glu Ser Gln His Pro Ser Asn Glu Ser Gly Asp
50                      55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
                100                 105                 110

His Ser Asn Cys Val Ser Phe Glu Cys Lys Thr Asp Pro Gly Val Phe
            115                 120                 125

Ile Gly Val Lys Asp Asn His Leu Ala Leu Ile Lys Val Asp Ser Ser
        130                 135                 140

Glu Asn Leu Cys Thr Glu Asn Ile Leu Phe Lys Leu Ser Glu Thr
145                 150                 155
```

<210> SEQ ID NO 6
<211> LENGTH: 255
<212> TYPE: PRT
<213> ORGANISM: homo sapiens

<400> SEQUENCE: 6

```
Met Gln Pro Leu Leu Leu Leu Ala Phe Leu Leu Pro Thr Gly Ala
1               5                   10                  15

Glu Ala Gly Glu Ile Ile Gly Gly Arg Glu Ser Arg Pro His Ser Arg
            20                  25                  30

Pro Tyr Met Ala Tyr Leu Gln Ile Gln Ser Pro Ala Gly Gln Ser Arg
        35                  40                  45

Cys Gly Gly Phe Leu Val Arg Glu Asp Phe Val Leu Thr Ala Ala His
50                  55                  60

Cys Trp Gly Ser Asn Ile Asn Val Thr Leu Gly Ala His Asn Ile Gln
65                  70                  75                  80

Arg Arg Glu Asn Thr Gln Gln His Ile Thr Ala Arg Ala Ile Arg
                85                  90                  95

His Pro Gln Tyr Asn Gln Arg Thr Ile Gln Asn Asp Ile Met Leu Leu
            100                 105                 110

Gln Leu Ser Arg Arg Val Arg Arg Asn Arg Asn Val Asn Pro Val Ala
        115                 120                 125

Leu Pro Arg Ala Gln Glu Gly Leu Arg Pro Gly Thr Leu Cys Thr Val
130                 135                 140

Ala Gly Trp Gly Arg Val Ser Met Arg Arg Gly Thr Asp Thr Leu Arg
145                 150                 155                 160

Glu Val Gln Leu Arg Val Gln Arg Asp Arg Gln Cys Leu Arg Ile Phe
                165                 170                 175

Gly Ser Tyr Asp Pro Arg Arg Gln Ile Cys Val Gly Asp Arg Arg Glu
            180                 185                 190

Arg Lys Ala Ala Phe Lys Gly Asp Ser Gly Gly Pro Leu Leu Cys Asn
        195                 200                 205

Asn Val Ala His Gly Ile Val Ser Tyr Gly Lys Ser Ser Gly Val Pro
```

```
                210                 215                 220
Pro Glu Val Phe Thr Arg Val Ser Ser Phe Leu Pro Trp Ile Arg Thr
225                 230                 235                 240

Thr Met Arg Ser Phe Lys Leu Leu Asp Gln Met Glu Thr Pro Leu
                245                 250                 255
```

<210> SEQ ID NO 7
<211> LENGTH: 256
<212> TYPE: PRT
<213> ORGANISM: homo sapiens

<400> SEQUENCE: 7

```
Met Ala His Arg Pro Pro Ser Pro Ala Leu Ala Ser Val Leu Leu Ala
1               5                   10                  15

Leu Leu Leu Ser Gly Ala Ala Arg Ala Ala Glu Ile Val Gly Gly His
                20                  25                  30

Glu Ala Gln Pro His Ser Arg Pro Tyr Met Ala Ser Leu Gln Met Arg
                35                  40                  45

Gly Asn Pro Gly Ser His Phe Cys Gly Gly Thr Leu Ile His Pro Ser
            50                  55                  60

Phe Val Leu Thr Ala Ala His Cys Leu Arg Asp Ile Pro Gln Arg Leu
65                  70                  75                  80

Val Asn Val Val Leu Gly Ala His Asn Val Arg Thr Gln Glu Pro Thr
                85                  90                  95

Gln Gln His Phe Ser Val Ala Gln Val Phe Leu Asn Asn Tyr Asp Ala
                100                 105                 110

Glu Asn Lys Leu Asn Asp Val Leu Leu Ile Gln Leu Ser Ser Pro Ala
                115                 120                 125

Asn Leu Ser Ala Ser Val Ala Thr Val Gln Leu Pro Gln Gln Asp Gln
            130                 135                 140

Pro Val Pro His Gly Thr Gln Cys Leu Ala Met Gly Trp Gly Arg Val
145                 150                 155                 160

Gly Ala His Asp Pro Pro Ala Gln Val Leu Gln Glu Leu Asn Val Thr
                165                 170                 175

Val Val Thr Phe Phe Cys Arg Pro His Asn Ile Cys Thr Phe Val Pro
                180                 185                 190

Arg Arg Lys Ala Gly Ile Cys Phe Gly Asp Ser Gly Gly Pro Leu Ile
                195                 200                 205

Cys Asp Gly Ile Ile Gln Gly Ile Asp Ser Phe Val Ile Trp Gly Cys
            210                 215                 220

Ala Thr Arg Leu Phe Pro Asp Phe Phe Thr Arg Val Ala Leu Tyr Val
225                 230                 235                 240

Asp Trp Ile Arg Ser Thr Leu Arg Arg Val Glu Ala Lys Gly Arg Pro
                245                 250                 255
```

<210> SEQ ID NO 8
<211> LENGTH: 267
<212> TYPE: PRT
<213> ORGANISM: homo sapiens

<400> SEQUENCE: 8

```
Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
                20                  25                  30

Gly Arg Arg Ala Arg Pro His Ala Trp Pro Phe Met Val Ser Leu Gln
```

|  | | 35 | | | 40 | | | 45 | | | |
|---|---|---|---|---|---|---|---|---|---|---|---|

Leu Arg Gly Gly His Phe Cys Gly Ala Thr Leu Ile Ala Pro Asn Phe
 50                        55                     60

Val Met Ser Ala Ala His Cys Val Ala Asn Val Asn Val Arg Ala Val
 65                     70                     75                     80

Arg Val Val Leu Gly Ala His Asn Leu Ser Arg Arg Glu Pro Thr Arg
                    85                     90                     95

Gln Val Phe Ala Val Gln Arg Ile Phe Glu Asn Gly Tyr Asp Pro Val
            100                    105                    110

Asn Leu Leu Asn Asp Ile Val Ile Leu Gln Leu Asn Gly Ser Ala Thr
            115                    120                    125

Ile Asn Ala Asn Val Gln Val Ala Gln Leu Pro Ala Gln Gly Arg Arg
130                    135                    140

Leu Gly Asn Gly Val Gln Cys Leu Ala Met Gly Trp Gly Leu Leu Gly
145                    150                    155                    160

Arg Asn Arg Gly Ile Ala Ser Val Leu Gln Glu Leu Asn Val Thr Val
                    165                    170                    175

Val Thr Ser Leu Cys Arg Arg Ser Asn Val Cys Thr Leu Val Arg Gly
            180                    185                    190

Arg Gln Ala Gly Val Cys Phe Gly Asp Ser Gly Ser Pro Leu Val Cys
            195                    200                    205

Asn Gly Leu Ile His Gly Ile Ala Ser Phe Val Arg Gly Gly Cys Ala
210                    215                    220

Ser Gly Leu Tyr Pro Asp Ala Phe Ala Pro Val Ala Gln Phe Val Asn
225                    230                    235                    240

Trp Ile Asp Ser Ile Ile Gln Arg Ser Glu Asp Asn Pro Cys Pro His
                    245                    250                    255

Pro Arg Asp Pro Asp Pro Ala Ser Arg Thr His
            260                    265

<210> SEQ ID NO 9
<211> LENGTH: 528
<212> TYPE: DNA
<213> ORGANISM: homo sapiens

<400> SEQUENCE: 9

```
gcctttggta tatcagggg t ccagaaatat actagagcac ttcatgattc aagtatcaca    60
ggaatttcac ctattacaga gtatcttgct tctctaagca catacaatga tcaatccatt   120
acttttgctt tggaggatga aagttatgag atatatgttg aagacttgaa aaagatgaa    180
aagaaagata aggtgttact gagttactat gagtctcaac acccctcaaa tgaatcaggt   240
gacggtgttg atggtaagat gttaatggta accctgagtc ctacaaaaga cttctggttg   300
catgccaaca acaaggaaca ctctgtggag ctccataagt gtgaaaaacc actgccagac   360
caggccttct tgtccttca taatatgcac tccaactgtg tttcatttga atgcaagact   420
gatcctggag tgtttatagg tgtaaaggat aatcatcttg ctctgattaa agtagactct   480
tctgagaatt tgtgtactga aaatatcttg tttaagctct ctgaaact              528
```

<210> SEQ ID NO 10
<211> LENGTH: 516
<212> TYPE: DNA
<213> ORGANISM: homo sapiens

<400> SEQUENCE: 10

```
tcaggggtcc agaaatatac tagagcactt catgattcaa gtatcacagg aatttcacct    60
```

```
attacagagt atcttgcttc tctaagcaca tacaatgatc aatccattac ttttgctttg      120
gaggatgaaa gttatgagat atatgttgaa gacttgaaaa agatgaaaaa gaaagataag      180
gtgttactga gttactatga gtctcaacac ccctcaaatg aatcaggtga cggtgttgat      240
ggtaagatgt taatggtaac cctgagtcct acaaaagact tctggttgca tgccaacaac      300
aaggaacact ctgtggagct ccataagtgt gaaaaaccac tgccagacca ggccttcttt      360
gtccttcata atatgcactc caactgtgtt tcatttgaat gcaagactga tcctggagtg      420
tttataggtg taaaggataa tcatcttgct ctgattaaag tagactcttc tgagaatttg      480
tgtactgaaa atatcttgtt taagctctct gaaact                               516

<210> SEQ ID NO 11
<211> LENGTH: 486
<212> TYPE: DNA
<213> ORGANISM: homo sapiens

<400> SEQUENCE: 11
catgattcaa gtatcacagg aatttcacct attacagagt atcttgcttc tctaagcaca       60
tacaatgatc aatccattac ttttgctttg gaggatgaaa gttatgagat atatgttgaa      120
gacttgaaaa agatgaaaaa gaaagataag gtgttactga gttactatga gtctcaacac      180
ccctcaaatg aatcaggtga cggtgttgat ggtaagatgt taatggtaac cctgagtcct      240
acaaaagact tctggttgca tgccaacaac aaggaacact ctgtggagct ccataagtgt      300
gaaaaaccac tgccagacca ggccttcttt gtccttcata atatgcactc caactgtgtt      360
tcatttgaat gcaagactga tcctggagtg tttataggtg taaaggataa tcatcttgct      420
ctgattaaag tagactcttc tgagaatttg tgtactgaaa atatcttgtt taagctctct      480
gaaact                                                                486

<210> SEQ ID NO 12
<211> LENGTH: 556
<212> TYPE: PRT
<213> ORGANISM: homo sapiens

<400> SEQUENCE: 12

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
                20                  25                  30

Ile Val Arg Cys Pro Arg Gln Gly Lys Pro Ser Tyr Thr Val Asp Trp
            35                  40                  45

Tyr Tyr Ser Gln Thr Asn Lys Ser Ile Pro Thr Gln Glu Arg Asn Arg
        50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
                100                 105                 110

Val Pro Asp Tyr Leu Met Tyr Ser Thr Val Ser Gly Ser Glu Lys Asn
            115                 120                 125

Ser Lys Ile Tyr Cys Pro Thr Ile Asp Leu Tyr Asn Trp Thr Ala Pro
        130                 135                 140

Leu Glu Trp Phe Lys Asn Cys Gln Ala Leu Gln Gly Ser Arg Tyr Arg
```

-continued

```
            145                 150                 155                 160
        Ala His Lys Ser Phe Leu Val Ile Asp Asn Val Met Thr Glu Asp Ala
                        165                 170                 175

Gly Asp Tyr Thr Cys Lys Phe Ile His Asn Glu Asn Gly Ala Asn Tyr
                        180                 185                 190

Ser Val Thr Ala Thr Arg Ser Phe Thr Val Lys Asp Glu Gln Gly Phe
                        195                 200                 205

Ser Leu Phe Pro Val Ile Gly Ala Pro Ala Gln Asn Glu Ile Lys Glu
            210                 215                 220

Val Glu Ile Gly Lys Asn Ala Asn Leu Thr Cys Ser Ala Cys Phe Gly
        225                 230                 235                 240

Lys Gly Thr Gln Phe Leu Ala Ala Val Leu Trp Gln Leu Asn Gly Thr
                        245                 250                 255

Lys Ile Thr Asp Phe Gly Glu Pro Arg Ile Gln Gln Glu Glu Gly Gln
                        260                 265                 270

Asn Gln Ser Phe Ser Asn Gly Leu Ala Cys Leu Asp Met Val Leu Arg
                        275                 280                 285

Ile Ala Asp Val Lys Glu Glu Asp Leu Leu Leu Gln Tyr Asp Cys Leu
            290                 295                 300

Ala Leu Asn Leu His Gly Leu Arg Arg His Thr Val Arg Leu Ser Arg
        305                 310                 315                 320

Lys Asn Pro Ile Asp His His Ser Ile Tyr Cys Ile Ile Ala Val Cys
                        325                 330                 335

Ser Val Phe Leu Met Leu Ile Asn Val Leu Val Ile Ile Leu Lys Met
                        340                 345                 350

Phe Trp Ile Glu Ala Thr Leu Leu Trp Arg Asp Ile Ala Lys Pro Tyr
                        355                 360                 365

Lys Thr Arg Asn Asp Gly Lys Leu Tyr Asp Ala Tyr Val Val Tyr Pro
                        370                 375                 380

Arg Asn Tyr Lys Ser Ser Thr Asp Gly Ala Ser Arg Val Glu His Phe
        385                 390                 395                 400

Val His Gln Ile Leu Pro Asp Val Leu Glu Asn Lys Cys Gly Tyr Thr
                        405                 410                 415

Leu Cys Ile Tyr Gly Arg Asp Met Leu Pro Gly Glu Asp Val Val Thr
                        420                 425                 430

Ala Val Glu Thr Asn Ile Arg Lys Ser Arg His Ile Phe Ile Leu
                        435                 440                 445

Thr Pro Gln Ile Thr His Asn Lys Glu Phe Ala Tyr Glu Gln Glu Val
            450                 455                 460

Ala Leu His Cys Ala Leu Ile Gln Asn Asp Ala Lys Val Ile Leu Ile
        465                 470                 475                 480

Glu Met Glu Ala Leu Ser Glu Leu Asp Met Leu Gln Ala Glu Ala Leu
                        485                 490                 495

Gln Asp Ser Leu Gln His Leu Met Lys Val Gln Gly Thr Ile Lys Trp
                        500                 505                 510

Arg Glu Asp His Ile Ala Asn Lys Arg Ser Leu Asn Ser Lys Phe Trp
                        515                 520                 525

Lys His Val Arg Tyr Gln Met Pro Val Pro Ser Lys Ile Pro Arg Lys
                        530                 535                 540

Ala Ser Ser Leu Thr Pro Leu Ala Ala Gln Lys Gln
        545                 550                 555

<210> SEQ ID NO 13
```

```
<211> LENGTH: 328
<212> TYPE: PRT
<213> ORGANISM: homo sapiens

<400> SEQUENCE: 13

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325

<210> SEQ ID NO 14
<211> LENGTH: 5428
<212> TYPE: DNA
<213> ORGANISM: artificial
<220> FEATURE:
<223> OTHER INFORMATION: pcDNA3.1 (+) DNA sequence

<400> SEQUENCE: 14
```

-continued

```
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgagctcgg atccactagt ccagtgtggt ggaattctgc   960
agatatccag cacagtggcg gccgctcgag tctagagggc ccgtttaaac ccgctgatca  1020
gcctcgactg tgccttctag ttgccagcca tctgttgttt gcccctcccc cgtgccttcc  1080
ttgaccctgg aaggtgccac tcccactgtc ctttcctaat aaaatgagga aattgcatcg  1140
cattgtctga gtaggtgtca ttctattctg gggggtgggg tggggcagga cagcaagggg  1200
gaggattggg aagacaatag caggcatgct ggggatgcgg tgggctctat ggcttctgag  1260
gcggaaagaa ccagctgggg ctctaggggg tatccccacg cgccctgtag cggcgcatta  1320
agcgcggcgg gtgtggtggt tacgcgcagc gtgaccgcta cacttgccag cgccctagcg  1380
cccgctcctt tcgctttctt cccttccttt ctcgccacgt tcgccggctt tccccgtcaa  1440
gctctaaatc gggggctccc tttagggttc cgatttagtg ctttacggca cctcgacccc  1500
aaaaaacttg attagggtga tggttcacgt agtgggccat cgccctgata cggttttttt  1560 cgcccttga cgttggagtc cacgttcttt aatagtggac tcttgttcca aactggaaca  1620
acactcaacc ctatctcggt ctattctttt gatttataag ggattttgcc gatttcggcc  1680
tattggttaa aaaatgagct gatttaacaa aaatttaacg cgaattaatt ctgtggaatg  1740
tgtgtcagtt agggtgtgga agtccccag gctccccagc aggcagaagt atgcaaagca  1800
tgcatctcaa ttagtcagca accaggtgtg gaaagtcccc aggctcccca gcaggcagaa  1860
gtatgcaaag catgcatctc aattagtcag caaccatagt cccgccccta actccgccca  1920
tcccgcccct aactccgccc agttccgccc attctccgcc ccatggctga ctaattttt  1980 ttatttatgc agaggccgag gccgcctctg cctctgagct attccagaag tagtgaggag  2040
gcttttttgg aggcctaggc ttttgcaaaa agctcccggg agcttgtata tccattttcg  2100
gatctgatca agacagga tgaggatcgt ttcgcatgat tgaacaagat ggattgcacg  2160
caggttctcc ggccgcttgg gtggagaggc tattcggcta tgactgggca acagacaa  2220 tcggctgctc tgatgccgcc gtgttccggc tgtcagcgca ggggcgcccg gttcttttg  2280 tcaagaccga cctgtccggt gccctgaatg aactgcagga cgaggcagcg cggctatcgt  2340
ggctggccac gacgggcgtt ccttgcgcag ctgtgctcga cgttgtcact gaagcgggaa  2400
```

```
gggactggct gctattgggc gaagtgccgg ggcaggatct cctgtcatct caccttgctc    2460
ctgccgagaa agtatccatc atggctgatg caatgcggcg gctgcatacg cttgatccgg    2520
ctacctgccc attcgaccac caagcgaaac atcgcatcga gcgagcacgt actcggatgg    2580
aagccggtct tgtcgatcag gatgatctgg acgaagagca tcaggggctc gcgccagccg    2640
aactgttcgc caggctcaag gcgcgcatgc ccgacggcga ggatctcgtc gtgacccatg    2700
gcgatgcctg cttgccgaat atcatggtgg aaaatggccg cttttctgga ttcatcgact    2760
gtggccggct gggtgtggcg gaccgctatc aggacatagc gttggctacc cgtgatattg    2820
ctgaagagct tggcggcgaa tgggctgacc gcttcctcgt gctttacggt atcgccgctc    2880
ccgattcgca gcgcatcgcc ttctatcgcc ttcttgacga gttcttctga gcgggactct    2940
ggggttcgaa atgaccgacc aagcgacgcc caacctgcca tcacgagatt tcgattccac    3000
cgccgccttc tatgaaaggt tgggcttcgg aatcgttttc cgggacgccg gctggatgat    3060
cctccagcgc ggggatctca tgctggagtt cttcgcccac cccaacttgt ttattgcagc    3120
ttataatggt tacaaataaa gcaatagcat cacaaatttc acaaataaag catttttttc    3180
actgcattct agttgtggtt tgtccaaact catcaatgta tcttatcatg tctgtatacc    3240
gtcgacctct agctagagct tggcgtaatc atggtcatag ctgtttcctg tgtgaaattg    3300
ttatccgctc acaattccac acaacatacg agccggaagc ataaagtgta aagcctgggg    3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcagggga    3600
taacgcagga agaacatgt gagcaaaagg ccagcaaaag gccaggaacc gtaaaaaggc    3660
cgcgttgctg gcgttttcc ataggctccg cccccctgac gagcatcaca aaaatcgacg    3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca tagctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc caacccggta agacacgact tatcgccact    4020
ggcagcagcc actggtaaca ggattagcag agcgaggtat gtaggcggtg ctacagagtt    4080
cttgaagtgg tggcctaact acggctacac tagaagaaca gtatttggta tctgcgctct    4140
gctgaagcca gttaccttcg gaaaaagagt tggtagctct tgatccggca aacaaaccac    4200
cgctggtagc ggtttttttg tttgcaagca gcagattacg cgcagaaaaa aaggatctca    4260
agaagatcct ttgatctttt ctacggggtc tgacgctcag tggaacgaaa actcacgtta    4320
agggattttg gtcatgagat tatcaaaaag gatcttcacc tagatccttt taaattaaaa    4380
atgaagtttt aaatcaatct aaagtatata tgagtaaact tggtctgaca gttaccaatg    4440
cttaatcagt gaggcaccta tctcagcgat ctgtctattt cgttcatcca tagttgcctg    4500
actccccgtc gtgtagataa ctacgatacg ggagggctta ccatctggcc ccagtgctgc    4560
aatgataccg cgagacccac gctcaccggc tccagattta tcagcaataa accagccagc    4620
cggaagggcc gagcgcagaa gtggtcctgc aactttatcc gcctccatcc agtctattaa    4680
ttgttgccgg gaagctagag taagtagttc gccagttaat agtttgcgca acgttgttgc    4740
```

```
cattgctaca ggcatcgtgg tgtcacgctc gtcgtttggt atggcttcat tcagctccgg    4800
ttcccaacga tcaaggcgag ttacatgatc ccccatgttg tgcaaaaaag cggttagctc    4860
cttcggtcct ccgatcgttg tcagaagtaa gttggccgca gtgttatcac tcatggttat    4920
ggcagcactg cataattctc ttactgtcat gccatccgta agatgctttt ctgtgactgg    4980
tgagtactca accaagtcat tctgagaata gtgtatgcgg cgaccgagtt gctcttgccc    5040
ggcgtcaata cgggataata ccgcgccaca tagcagaact ttaaaagtgc tcatcattgg    5100
aaaacgttct cggggcgaaa actctcaag gatcttaccg ctgttgagat ccagttcgat    5160
gtaacccact cgtgcaccca actgatcttc agcatctttt actttcacca gcgtttctgg    5220
gtgagcaaaa acaggaaggc aaaatgccgc aaaaaaggga ataagggcga cacggaaatg    5280
ttgaatactc atactcttcc tttttcaata ttattgaagc atttatcagg gttattgtct    5340
catgagcgga tacatatttg aatgtattta gaaaaataaa caaatagggg ttccgcgcac    5400
atttccccga aaagtgccac ctgacgtc                                      5428
```

<210> SEQ ID NO 15
<211> LENGTH: 178
<212> TYPE: PRT
<213> ORGANISM: Homo sapiens

<400> SEQUENCE: 15

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp
```

<210> SEQ ID NO 16
<211> LENGTH: 92
<212> TYPE: PRT
<213> ORGANISM: Homo sapiens

<400> SEQUENCE: 16

```
Gly Lys Met Leu Met Val Thr Leu Ser Pro Thr Lys Asp Phe Trp Leu
1               5                   10                  15

His Ala Asn Asn Lys Glu His Ser Val Glu Leu His Lys Cys Glu Lys
```

```
                     20                  25                  30
Pro Leu Pro Asp Gln Ala Phe Phe Val Leu His Asn Met His Ser Asn
            35                  40                  45

Cys Val Ser Phe Glu Cys Lys Thr Asp Pro Gly Val Phe Ile Gly Val
            50                  55                  60

Lys Asp Asn His Leu Ala Leu Ile Lys Val Asp Ser Ser Glu Asn Leu
65                      70                  75                  80

Cys Thr Glu Asn Ile Leu Phe Lys Leu Ser Glu Thr
                    85                  90
```